United States Patent
Chang et al.

(10) Patent No.: US 11,681,610 B2
(45) Date of Patent: Jun. 20, 2023

(54) SYNTHESIZING DATA BASED ON TOPIC MODELING FOR TRAINING AND TESTING MACHINE LEARNING SYSTEMS

(71) Applicant: Data-Core Systems, Inc., Philadelphia, PA (US)

(72) Inventors: Sin-Min Chang, Shelton, CT (US); Anshuman Narayan, Philadelphia, PA (US); Jishnu Bhattacharyya, Philadelphia, PA (US); Pradeep K. Banerjee, Bristol, PA (US); Rathi Dasgupta, Chicago, IL (US)

(73) Assignee: Data-Core Systems, Inc., Philadelphia, PA (US)

(*) Notice: Subject to any disclaimer, the term of this patent is extended or adjusted under 35 U.S.C. 154(b) by 233 days.

(21) Appl. No.: 17/318,083

(22) Filed: May 12, 2021

(65) Prior Publication Data

US 2021/0357316 A1    Nov. 18, 2021

Related U.S. Application Data

(60) Provisional application No. 63/024,103, filed on May 13, 2020.

(51) Int. Cl.
| | |
|---|---|
| *G06F 11/36* | (2006.01) |
| *G06N 20/00* | (2019.01) |
| *G16H 50/20* | (2018.01) |
| *G16H 70/60* | (2018.01) |
| *G16H 70/20* | (2018.01) |
| *G06Q 40/08* | (2012.01) |

(52) U.S. Cl.
CPC ...... *G06F 11/3692* (2013.01); *G06F 11/3684* (2013.01); *G06N 20/00* (2019.01); *G06Q 40/08* (2013.01); *G16H 50/20* (2018.01); *G16H 70/20* (2018.01); *G16H 70/60* (2018.01)

(58) Field of Classification Search
CPC .. G06F 11/36; G06F 11/3692; G06F 11/3684; G06N 20/00
See application file for complete search history.

(56) References Cited

U.S. PATENT DOCUMENTS

| | | | |
|---|---|---|---|
| 10,803,399 B1* | 10/2020 | Cohen | G06F 16/93 |
| 11,315,196 B1* | 4/2022 | Narayan | G06F 18/285 |
| 2012/0078895 A1* | 3/2012 | Chu-Carroll | G06F 16/332 |
| | | | 707/E17.014 |
| 2019/0155947 A1* | 5/2019 | Chu | G06F 16/358 |
| 2020/0242623 A1* | 7/2020 | Savir | G06V 10/82 |

(Continued)

*Primary Examiner* — Kamini B Patel
(74) *Attorney, Agent, or Firm* — Akerman LLP

(57) ABSTRACT

Systems and methods for generating a dataset of synthesized data items from a dataset of original data items are disclosed herein. Some embodiments include (i) selecting an original data item from the dataset of original data items, where each original data item (a) comprises a combination of first-type codes and second-type codes, and (b) is associated with a topic in a topic model; and (ii) generating a synthesized data item based on the original data item and the topic associated with the original data item, where the synthesized data item comprises a combination of first-type codes and second-type codes that differs from the combination of first-type codes and second-type codes in the original data item by one first-type code or one second-type code.

21 Claims, 11 Drawing Sheets

(56) References Cited

U.S. PATENT DOCUMENTS

| | | | |
|---|---|---|---|
| 2021/0191990 A1* | 6/2021 | Shi | G06F 16/9014 |
| 2022/0092086 A1* | 3/2022 | Tumpic | G06N 5/01 |
| 2022/0207302 A1* | 6/2022 | Kato | G06F 18/214 |
| 2022/0366133 A1* | 11/2022 | Potash | G06N 3/08 |

* cited by examiner

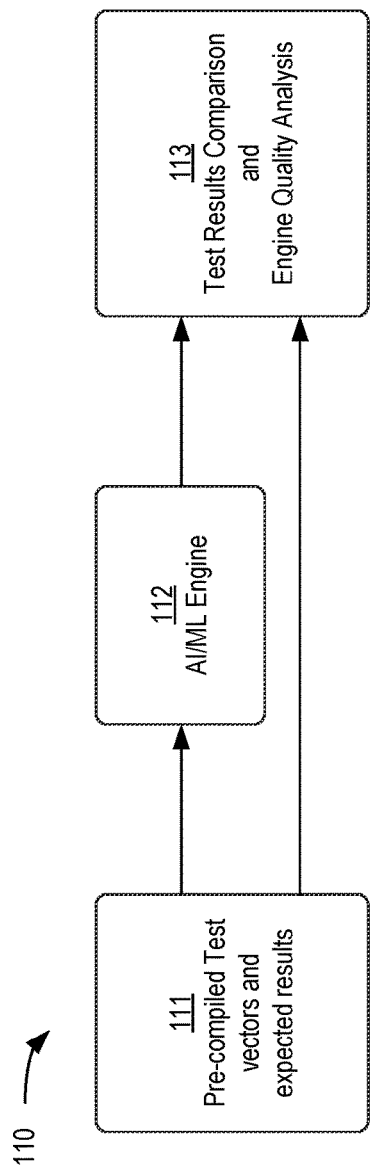
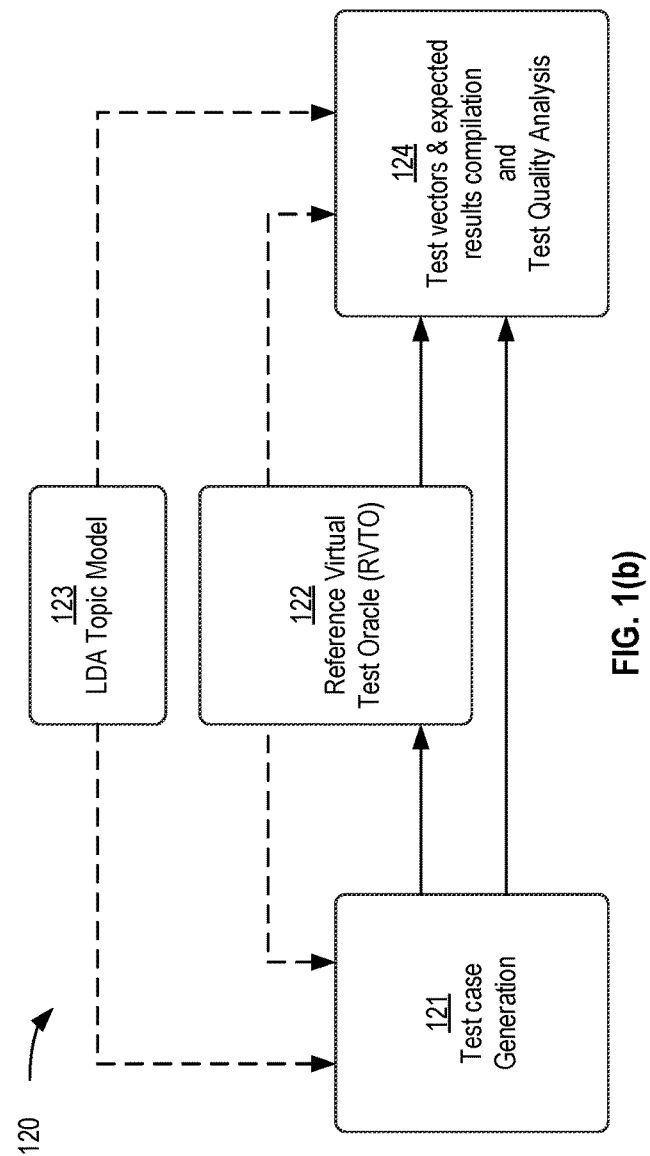
FIG. 1(a)
FIG. 1(b)

SYNTHESIZING DATA BASED ON TOPIC MODELING FOR TRAINING AND TESTING MACHINE LEARNING SYSTEMS

CROSS-REFERENCE TO RELATED APPLICATIONS

The present application claims priority to U.S. Provisional Application No. 63/024,103 titled "Implementing Differential Testing with Topic Modeling for Machine Learning Systems," filed on May 13, 2020, and currently pending. The entire contents of U.S. Provisional Application No. 63/024, 103 are incorporated herein by reference.

The present application also incorporates by reference the entire contents of (i) U.S. Provisional Application No. 62/943,217 titled "Novel Medical Claim Inspection System Using Combined Rules and AI/ML Engine," filed on Dec. 3, 2019; (ii) U.S. application Ser. No. 17/111,123 titled "Systems and method for selecting a classification of input data from multiple classification systems" filed on Dec. 3, 2020; (iii) U.S. application Ser. No. 17/147,054 titled "Synthesized invalid insurance claims for training an Artificial Intelligence/Machine Learning Model," filed on Jan. 12, 2021; and (iv) U.S. application Ser. No. 17/156,768 titled "Systems and methods for identifying and curing anomalies in insurance claims," filed on Jan. 25, 2021.

SUMMARY

Traditional software testing is typically based on a "white-box" approach in which the internal structure, design, and coding of software is tested to verify the flow of input data to output results and to improve the design, usability, and security of the software. In white box testing, the software code is visible to testers for testing and verification of the software.

However, the traditional "white box" software testing approach is not practical (and sometimes not possible) when testing and verifying the operation of Artificial Intelligence/Machine Learning (AI/ML) models, because the AI/ML models do not have a precisely formulated software code like a traditional software program. Thus, a completely different approach for testing neural network based AI/ML models is required. Instead of toggling the source code as with traditional testing approaches, pairs of test cases can be synthesized to generate differential tests to observe how the AI/ML model operates.

Differential testing, sometimes referred to a differential fuzzing, is a popular software testing technique that attempts to detect bugs and other anomalies by providing the same input to a series of similar applications (or to different implementations of the same application), and observing differences in their execution and/or outcomes. Differential testing complements traditional software testing because differential testing is well-suited to find semantic or logic bugs that do not exhibit explicit erroneous behaviors like crashes or assertion failures. For these reasons, differential testing can be an effective approach for testing and validating AI/ML models.

Aspects of the systems and methods disclosed herein include novel model-agnostic "black-box" differential testing techniques that include synthesizing tests for validating AI/ML models. One of the novel aspects of the differential testing approaches disclosed herein includes the use of a pre-processed topic model, such as a Latent Dirichlet Allocation (LDA) Topic Model. The topic model is created based on a collection of data before performing a train-test split procedure. In operation, the topic model (rather than the neural network implementation) is used to guide the generation of synthesized test data that is used to test and verify the operation of the AI/ML model. In some embodiments, an individual differential test includes of a pair of tests where the test inputs are related to each other with specific differences while the expected outputs represent two different outcomes. To create a pair of tests, some embodiments of the disclosed systems and methods include using data items selected from a dataset of training data as one of the tests for the differential pair. In operation, the classification of each data items in the training dataset is known. The other test of the in the differential pair is synthesized by adding/removing/replacing one of the inputs (e.g., in the context of insurance claims processing, a diagnosis code or a procedure code) of the "known" data item selected from the dataset of training data. Multiple sets of choices for which input to add/remove/replace can be created by classifying the known data item via topic modeling. Instead of looking for a suitable replacement input from all potential inputs (e.g., in the context of insurance claims processing, selecting a diagnosis code or procedure code from the entire diagnosis code and procedure code space, which could be over 100,000 different candidates), the approaches disclosed herein simplify the search for a suitable input to add/remove/replace in the known data item by looking for the potential inputs to add/remove/replace in the known data item from the inputs used only by data items within a classified subset of data items identified using topic modeling.

This novel strategy reduces the search space substantially, thereby improving the operation of computing systems by, for example, (i) reducing computing time and resources required to generate suitable differential test pairs for testing and verifying the operation of AI/ML Engines, especially for AI/ML Engines configured to classify input data having ultra-high dimensionality, (ii) improving the efficiency of computing systems configured to generate testing data by allocating computing resources to generating "high quality" differential testing data for testing AI/ML Engines rather than wasting time generating differential testing data that has limited value for testing, and (iii) enabling more efficient use of computing systems configured to implement AI/ML models by in that testing an AI/ML model with higher quality differential testing data reduces the amount of time devoted to testing the AI/ML model, which in turn increases the amount of the time the AI/ML model can be used for classifying live data in a live production environment. Additionally, using the differential testing approaches disclosed herein also helps to identify strategies for supplemental training of AI/ML models, which help to improve the ability of the AI/ML models to classify input data more consistently and reliability.

In addition, some embodiments also include evaluating and analyzing the suitability and coverage of the generated differential test pairs on a per topic basis to ensure that the differential tests cover a broader range of topics and to identify (and in turn address) potential bias in testing.

The embodiments shown, disclosed, and described in the figures and specification are set forth only as examples. As such, those skilled in the art will appreciate that other arrangements and elements (e.g., machines, interfaces, functions, orders, and groupings of functions) can be used instead, and that some elements may be omitted altogether. Further, many of the elements shown and described herein are functional entities that may be implemented as discrete or distributed components or in conjunction with other components, and in any suitable combination and location.

Various functions described herein as being performed by one or more entities may be carried out by hardware, firmware, and/or software (and any combination thereof). For example, one or more processors executing instructions stored in one or more tangible computer-readable memory components may implement one or more of the features and functions described herein.

Some embodiments comprise tangible, non-transitory computer readable media comprising instructions encoded thereon, where the instructions, when executed by one or more processors, cause one or more computing devices and/or systems to execute one or more methods comprising a series of one or more processes and/or sub-processes to perform the functions disclosed and/or described herein.

In some embodiments, the sub-processes (or perhaps functions thereof) may be performed successively (or serially), simultaneously (or in parallel), or intermittently with other sub-processes (or perhaps functions thereof). Further, it is envisioned that some of the steps and/or functions of the sub-processes may be changed, may be substituted for, may be combined with other steps and/or functions of other sub-processors, or may be eliminated. Further, it is envisioned that some sub-processes and other disclosed methods may include additional steps not explicitly shown or described herein. The methods, processes, and sub-processes described herein are merely exemplary and those skilled in the art will recognize modifications that fall within the scope and spirit of the inventions and embodiments thereof disclosed and described herein.

One implementation of Data-Core Systems Inc.'s Denial Management System includes a combination of a Rules Engine and an Artificial Intelligence/Machine Learning (AI/ML) Engine configured to operate in concert to identify whether an insurance payer is likely to deny payment of an insurance claim. In operation, some of the denials are suitable for detection by a Rules Engine, for example, like the eligibility of a claim; some denials are more suitable for detection by using an AI/ML Engine, for example, like the consistency between diagnosis codes (associated with a medical diagnosis) and procedure codes (associated with a medical procedure) appearing in the insurance claim. Each insurance claim in general includes multiple codes and represents diverse characteristics of the claim and its associated medical diagnosis and procedure. The Denial Management System is configured to identify potential inconsistencies or errors in insurance claims that are likely to result in a denial of payment by examining the codes appearing in the insurance claims, including the diagnosis codes and procedure codes, and other information, including age, gender, etc., in the insurance claim. Because these inconsistencies or other errors in an insurance claim may result in a denial of payment by the payers, it is advantageous for healthcare service providers to identify (and correct) such inconsistencies and/or other errors in insurance claims before submitting the claims to a payer in order to avoid a loss or delay in receiving payment from the insurance payer.

However, analyzing insurance claims to identify inconsistencies and/or errors in an individual claim that may cause a payer to deny payment of the insurance claim is very complex and challenging because of all the different combinations of diagnosis codes and procedure codes that could possibly appear in an insurance claim. For example, currently there are more than 70,000 unique diagnosis codes and more than 25,000 unique procedure codes, and new diagnosis codes and new procedure codes are added all the time. In addition to the unique diagnosis codes and procedure codes, some diagnosis codes and procedure codes also have modifiers that must be analyzed as well.

The high number of combinations of potential diagnosis codes and procedure codes (along with the various modifiers relating to the diagnosis codes and procedure codes) makes it impractical to use only a Rules Engine to identify inconsistencies in an insurance claim. Enumerating all the possible rules to describe the causes of denial will be extremely cumbersome and almost impossible to manage. Managing rule changes and updates is also exceedingly difficult, with the complexity increasing as a function of the total number or rules implemented by the Rules Engine. To address the complexity and operational impracticality of analyzing insurance claims with a Rules Engine, the Denial Management System implemented by Data-Core Systems includes a combination of both a Rules Engine and an Artificial Intelligence (AI)/Machine Learning (ML) Engine configured to analyze insurance claims and identify inconsistencies and/or errors that are likely to cause a payer to deny payment of the insurance claim.

A Rules Engine can be implemented using a traditional software development architecture and methodology, and the quality and correctness of the implemented software functionality can be tested using traditional test methodologies and criteria. On the other hand, an AI/ML Engine typically cannot be tested with traditional methodologies and criteria like code coverage as readily as a Rules Engine because the behavior of the AI/ML Engine is governed by both the software model and the data that was used to "train" the software model. Because most of the software models for testing are based on common libraries and hidden from the developers and system integrators, the assumptions and the use of traditional white box testing approaches and criteria are generally not sufficient for testing the types of software models implemented by AI/ML Engine(s) used in complex machine learning applications such as insurance claim processing and analysis or other complex machine learning applications.

Some embodiments of the systems and methods disclosed and described herein implement a novel model-agnostic "black-box" differential testing technique to synthesize test data that can be used for validating an AI/ML Engine. A topic model (e.g. a Latent Dirichlet Allocation (LDA) Topic Model or other appropriate topic model) is created as a pre-processing step. The topic model is based on a "reference" dataset comprising data items (e.g., insurance claims) that have a known classification (e.g., where each insurance claim in the "reference" dataset is known to be either (i) acceptable for payment by an insurance payer or (ii) unacceptable for payment by the insurance payer, i.e., likely to be denied payment if submitted to the payer). In some embodiments, the reference dataset is split into two different subsets: (i) one subset for training and (ii) the other subset for testing. In operation, the topic model (e.g., an LDA model or other suitable topic model) is used to guide the generation of the synthesized test data instead of using the neural network implementation as a guide for generating the synthesized test data.

Differential testing, also known as differential fuzzing, is a popular software testing technique that attempts to detect bugs by providing the same input to a series of similar applications (or to different implementations of the same application) and observing differences in their execution and outcomes. Differential Testing involves using a pair of test data where inputs are related to each other with specific differences while expected outputs represent two different outcomes. A novel strategy is disclosed herein which relies on using the known and confirmed data (e.g., the reference dataset mentioned above) including the training data as a basis to generate differential tests instead of using the neural network implementation details for guiding the generation of synthesized test data.

In some embodiments, the pair of test data includes (i) one "reference" data item selected from the reference dataset (e.g., the known non-denial (good) or denial (bad) insurance claims) and (ii) a "synthesized" data item that is generated by adding, deleting, or replacing one or more components of the "reference" data item in the differential test pair. For example, in the context of insurance claims, the "synthesized" data item may correspond to a new "synthesized" insurance claim that is formed by replacing at least one of the Diagnosis Code(s) or Procedure Code(s) appearing in the "reference" insurance claim of the differential test pair on which the "synthesized" insurance claim is based. But rather than adding or removing a component of the "reference" data item by randomly selecting a component to add or delete, or replacing a component of the "reference" data item with another component selected at random from all possible components, the adding/deleting/replacement is based on a topic model. For example, in the context of insurance claims, to produce a "synthesized" insurance claim based on a "reference" insurance claim, a particular diagnosis code or procedure code can be added to the reference insurance claim, removed from the reference insurance claim, or replaced with a different diagnosis code or procedure code in the "reference" insurance claim based on the topic model instead of randomly adding/removing/replacing diagnosis and procedure codes from all possible diagnosis and procedure Codes. Multiple sets of choices can be created by classifying the data items in the reference dataset using the above mentioned topic model (e.g., a LDA Topic Model or other topic model). For example, in the context of insurance claims, instead of looking for a suitable replacement code (i.e., when replacing a diagnosis or procedure code in the "reference" insurance claim with a different diagnosis or procedure code) from the entire set diagnosis and procedure codes available (which is currently over 70,000 diagnosis codes and over 25,000 procedure codes), we instead only look for the replacement code from those used by a classified set of insurance claims identified using the topic model, as described in more detail herein. This novel strategy reduces the search space substantially and yields synthesized test data that is more effective at testing and/or training the AI/ML Engine to classify new input data as compared to prior approaches.

Additionally, incorrectly classifying an "invalid" data item as a "valid" data item is another problem that occurs in ultra-high dimensional data/code modeling. For example, in the insurance claim context, incorrectly classifying an insurance claim likely to be denied payment (i.e., a "bad" claim) as a claim that is likely to be approved for payment (i.e., a "good" claim) is generally referred to a "false denial." This type of "false denial" can occur for various reasons. This is especially true when the training data is "imbalanced," i.e., has more "valid" data items than "invalid" data items. For example, in the insurance context the training data is imbalanced when most of the insurance claims contained in the training are "non-denial" (i.e., good) insurance claims. Thus, in addition to synthesizing test data, some embodiments disclosed herein additionally relate to generating test vectors to detect gross false non-denial claims, sometimes referred to herein as Qualifying Denial Testing. The disclosed methods of Qualified Denial Testing leverage the topic model described above.

In operation, the quality/characteristics of the synthesized test data items are measured based not only on the characteristics of the test data items within the differential pair, but also based on a comparison with live data received by the AI/ML Engine for classification in post-deployment. Comparing the synthesized test data with live test data in this manner includes treating the live data a type of test data. For example, in the context of insurance claims, this comparison includes comparing the synthesized insurance claims with live insurance claims as described in further detail herein.

In the insurance claim processing context, when the payer denies an insurance claim that the AI/ML Engine previously classified as acceptable for payment (e.g., when the actual classification (denial) conflicts with the AI/ML engine's predicted classification), then the discrepancy between the actual and predicted classification is an indicator that the AI/ML could benefit from further training with additional training data added to the training dataset. On the other hand, even when the actual classification matches the predicted classification (e.g., when an insurance payer pays an insurance claim that AI/ML classified as "good"), there may still be an opportunity to improve the classification capabilities of the AI/ML engine. One reason why an insurance payer may have decided to pay an insurance claim could be attributed to so called "under coding" when an insurance coder becomes very conservative in his or her coding of insurance claims so as to avoid claim denial. Under coding is not good for the healthcare service provider because under coding potentially results in the healthcare provider charging for (and getting paid for) a different (and possibly lower cost) healthcare service than the actual healthcare service provided. Certain embodiments of some of the systems and methods disclosed herein also address this and other types of testing and measurement under post-deployment situations using topic models.

Further, the topic model described above can also be used for more general Train-Test Split applications. For example, instead of randomly selecting data items for inclusion in a test dataset from the entire collection of potential data items for use with the test dataset before the Train-Test Split, the random selection of data items for inclusion in the test dataset is performed on a per topic basis. In some embodiment, the topic modeling algorithm (e.g., LDA topic modeling or other suitable topic modeling) is applied to the entire collection of potential data items for use with the test data set to organize the entire collection of potential data items according to topic. And then, data items can be randomly selected from each topic. This approach helps to ensure that the data items in the testing data set are selected from all of the topics represented by the entire collection of data items from which the testing dataset is drawn from, thereby helping to avoid under representation or over representation of topics in the training dataset.

BRIEF DESCRIPTION OF THE DRAWINGS

FIG. 1(a) shows aspects of an example architecture for testing an AI/ML Engine according to some embodiments.

FIG. 1(b) shows aspects of an example architecture for generating synthesized test data for use with testing an AI/ML Engine according to some embodiments.

DETAILED DESCRIPTION OF THE DRAWINGS

Figure 2:
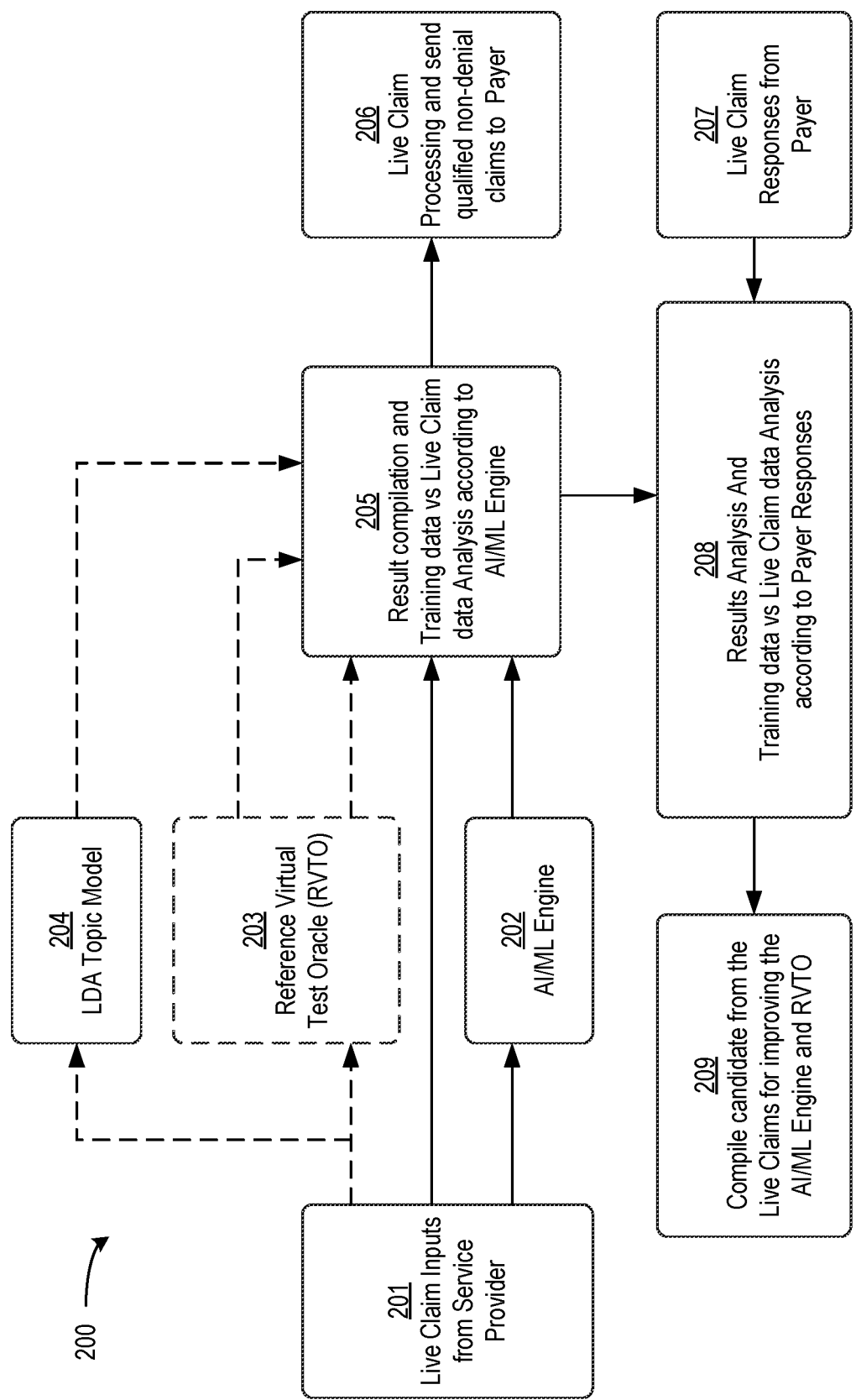
FIG. 2 shows aspects of an example architecture for testing an AI/ML Engine after initial deployment according to some embodiments.

Tests can be categorized into pre-deployment tests and post-deployment tests. FIG. 1(a) shows aspects of an example architecture 110 for testing an AI/ML Engine in a pre-deployment environment according to some embodiments. FIG. 1(b) shows aspects of an example architecture 120 for generating synthesized test data for use with testing an AI/ML Engine according to some embodiments, including an architecture for compiling differential test vectors shown in block 111 of FIG. 1(a). FIG. 2 shows aspects of an example architecture 200 for testing an AI/ML Engine after initial deployment, including a post-deployment test environment.

Example architecture 110 shown in FIG. 1(a) includes block 110, block 112, and block 113. In FIG. 1(a), block 110 represents a test execution environment given an AI/ML Engine under test in a pre-deployment scenario. Pre-deployment tests for a targeted software module are commonly used to test software quality. A similar architecture is also used for AI/ML Engine testing shown in FIG. 1(a).

Test vectors and expected results are pre-compiled in block 111 of example architecture 110 in FIG. 1(a).

Block 112 of example architecture 110 includes an AI/ML Engine. The expected results are compared with the output of the AI/ML Engine 112 and mismatches between the expected results and the actual results are detected at block 0113. The output of the AI/ML Engine 112 is not a binary value of either a "1" (e.g., valid) or "0" (e.g., invalid) classification. For example, in the context of insurance claim classification, a "1" may correspond to a classification of the insurance claim as a "non-denial" (i.e., an insurance claim that an insurance company will likely pay) whereas a "0" may correspond to a "denial" (i.e., an insurance claim that an insurance company will likely reject for payment). Instead, the AI/ML Engine outputs some value between 0 and 1. For example, a synthesized insurance claim might receive an output value of 0.6 from the AI/ML Engine, which might represent an "unknown" classification for the synthesized insurance claim. Thus, the output of the AI/ML Engine for a synthesized denial claim as its input could be acceptable for a range from "denial" to "low confident denial" while a synthesized non-denial claim could be identified to be "non-denial" to "low confident non-denial." Likewise, a value or score between a specific range (for example, 0.4 to 0.6) between "low confident denial" and "low confident non-denial" could be considered as "unknown," where "unknown" corresponds to a scenario where the AI/ML Engine is unable to classify the synthesized insurance claim as either a "denial" or a "non-denial" insurance claims. Such ranges are thresholds that can be provisioned by a user (or operator) or the AI/ML Engine, and different ranges/thresholds may be appropriate for different applications, e.g., insurance claims processing, image processing, text recognition, and so on.

Block 113 of example architecture 110 includes software for comparing test results and assessing the quality of the AI/ML Engine and/or the quality of the test data used for testing the AI/ML Engine. The quality of the AI/ML Engine can be evaluated based on a measure of the testing used to qualify the AI/ML Engine. If the AI/ML Engine is tested with a set of high-quality test data, then an AI/ML Engine that passes the testing should be a high-quality AI/ML Engine. In some embodiments, testing data for testing the AI/ML Engine can be selected from both (i) a dataset comprising known test data and (ii) a dataset comprising synthesized test data. In the insurance claim processing context, the known test data in some embodiments may include one or more of (i) insurance claims that are known to be "valid" insurance claims (sometimes referred to herein as "good" claims) that, if submitted to an insurance company for payment, the insurance company would very likely pay the insurance claim, (ii) insurance claims that are known to be "invalid" insurance claims (sometimes referred to herein as "bad" or "denial" claims) that, if submitted to an insurance company for payment, the insurance company would very likely deny payment of the insurance claim, (iii) synthesized "valid" insurance claims, and/or (iv) synthesized "invalid" insurance claims. In some embodiments, the synthesized test data is created from the known test data based on some additional knowledge about the known test data, e.g., based on topic modeling as described further herein.

For differential testing, test vectors representing the test data are organized as a sequence of test vector pairs, where each pair includes two consecutive related vectors of different expected results from the Module Under Test (MUT) which is an AI/ML Engine in this case. At block 113, the actual effectiveness of the differential testing with regard to test coverage and differential gap is analyzed as described in this disclosure. In practice, a differential pair having a smaller difference between the synthesized data item (e.g., a synthesized claim) and the known data item on which the synthesized data item is based (e.g., a known claim on which the synthesized claim was based) is better than a differential pair having a greater difference between the synthesized data item and the known data item on which the synthesized data item is based. The difference between the synthesized data item and the known data item on which the synthesized data item was based in the differential pair is known as the differential gap of the differential pair. The differential gap is a measure of the change (or difference between) the synthesized data item and its corresponding known data item.

Figure 3:
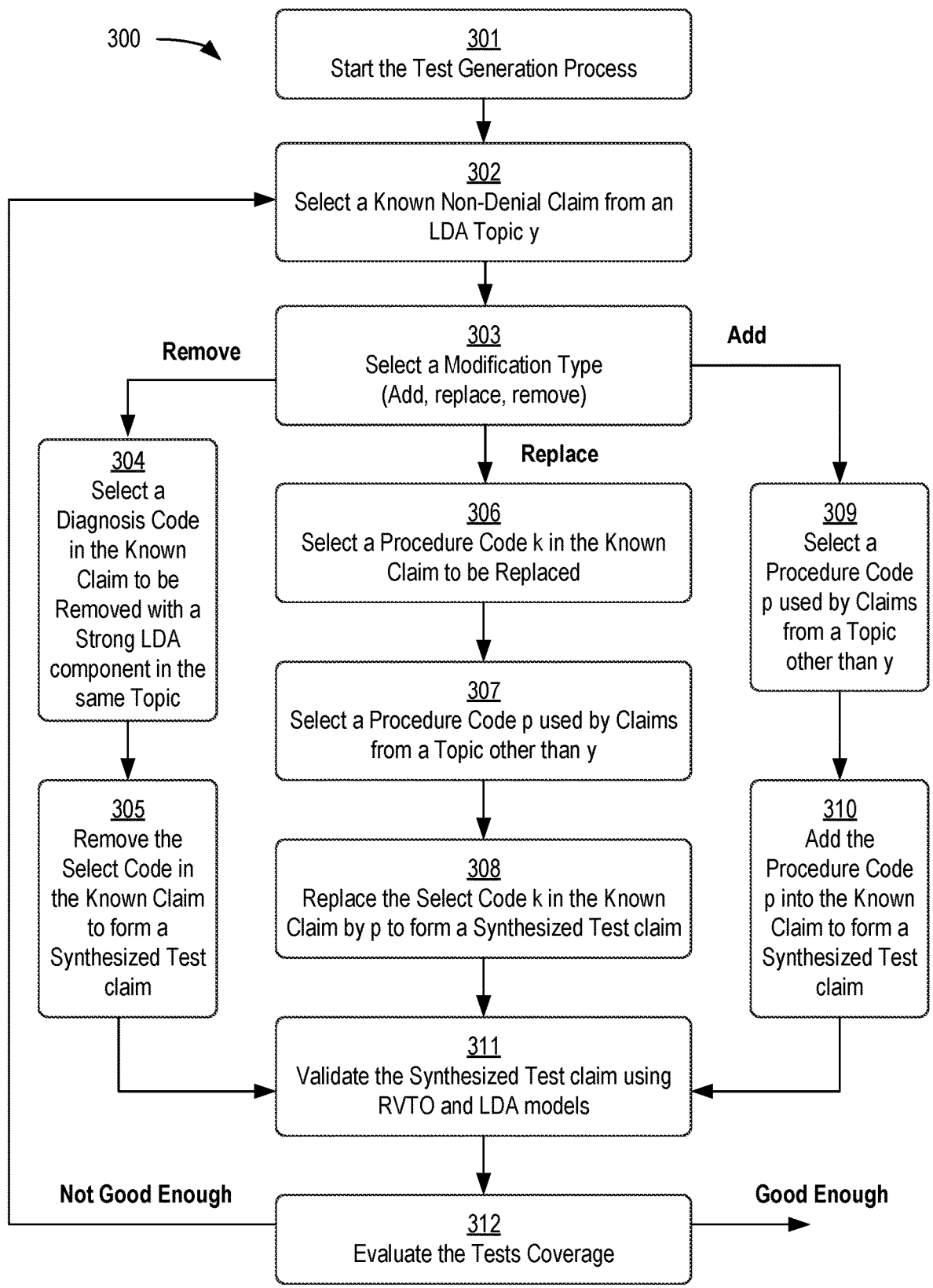
FIG. 3 shows aspects of an example process for generating a synthesized denial insurance claim using a known non-denial insurance claim according to some embodiments.
Figure 4:
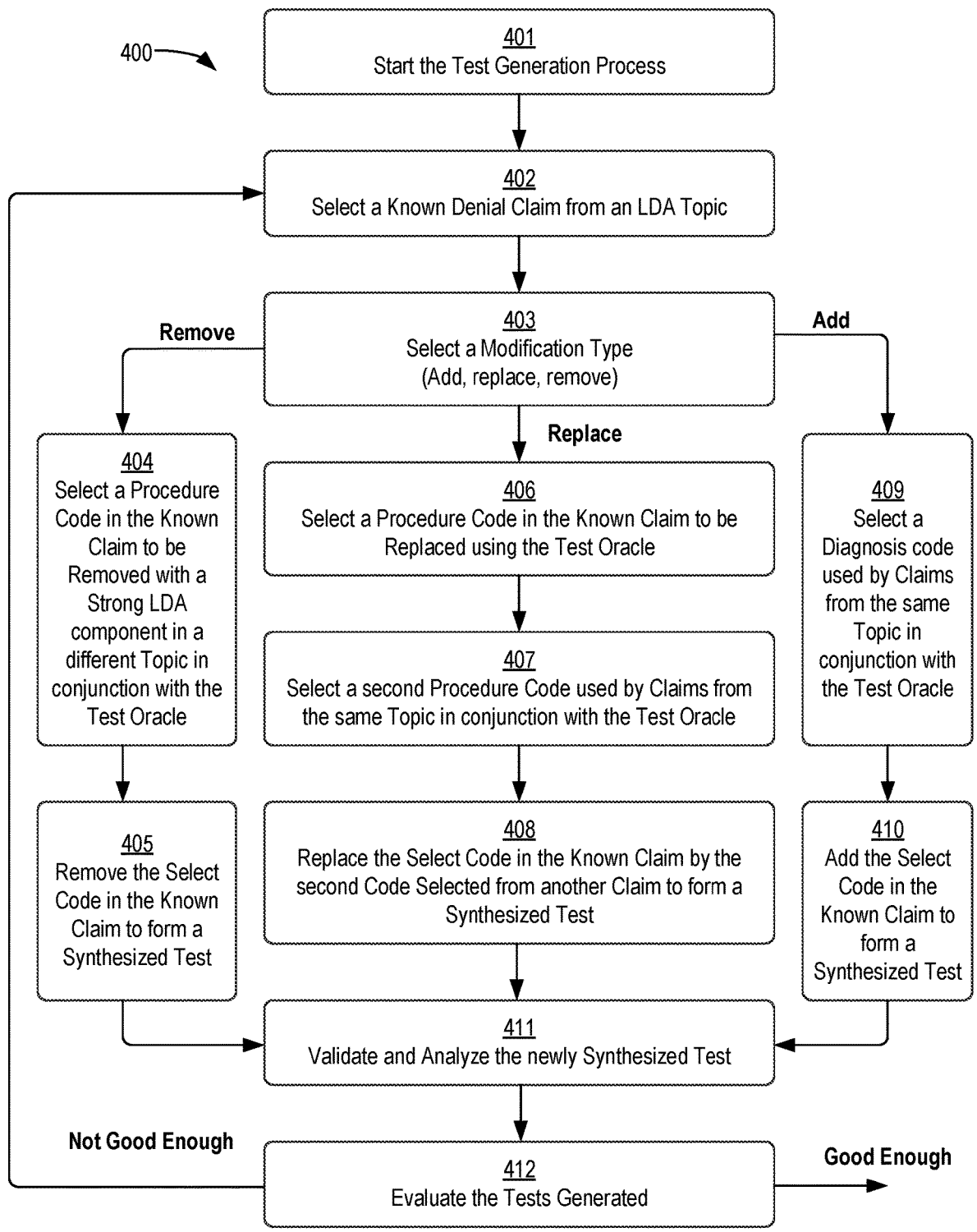
FIG. 4 shows aspects of an example process for generating a synthesized non-denial insurance claim using a known denial insurance claim according to some embodiments.

In some embodiments, Kullback-Leibler divergence (KL divergence) can be used to measure the differential gap between the data items within a differential test pair, as described further herein with respect to FIGS. 3 and 4. In operation, one goal of generating the synthesized data items is to produce high quality differential tests with an acceptable differential gap. In some embodiments, the measure of differential gap that is acceptable can be configured by a test program user.

FIG. 1(b) shows aspects of an example architecture 120 for generating synthesized test data for use with testing an AI/ML Engine according to some embodiments. Example architecture 120 in FIG. 1(b) includes a test generation block 121 that includes software for synthesizing the differential test vectors. In some embodiments, test generation block 121 also includes software for generating the qualifying denial testing data described above.

Example architecture 120 in FIG. 1(b) also includes a Reference Virtual Test Oracle (RVTO) in block 122, a topic model (e.g., a Latent Dirichlet Allocation (LDA) topic model or other suitable topic model) in block 123, and software for performing test vector compilation and quality analysis in block 124. Details of the functions performed by the software in blocks 121, 122, 123, and 124 are described in the following paragraphs. Additionally, aspects of the procedure for synthesizing differential test vectors for use in block 121 is shown in further detail in FIG. 3 and FIG. 4.

The Reference Virtual Test Oracle (RVTO) of block 122 is an information system and can take several forms. For example, in some embodiments, the RVTO comprises a database. In other embodiments, the RVTO comprises a matrix, such as a co-occurrence matrix as described herein. In operation, the system uses the RVTO to determine whether a synthesized data item has "passed" or "failed," for example, by determining whether the synthesized data item is represented in the RVTO.

The behavior of the AI/ML Engine at block 112 (which is the Module Under Test) can be predicted by querying the RVTO. The RVTO is commonly used for test vector generation and can be either an information system or a human domain expert. In the systems and methods disclosed and described herein, the RVTO is an information system. The RVTO at block 122 contains facts collected, e.g., outcomes of classifications of data items provided to the AI/ML Engine 112.

In some embodiments, the RVTO comprises a cooccurrence matrix that describes relationships among the attributes of the "known" data items stored therein. For example, in the insurance claim context wherein individual insurance claims include one or more diagnosis codes (corresponding to a medical diagnosis) and one or more procedure codes (corresponding to a medical procedure) the cooccurrence matrix comprises data relating whether and the extent to which each diagnosis code appears with each procedure code in each "known" individual insurance claim of the set of insurance claims that were used to create the RVTO. When a diagnosis code and a procedure code co-exist in a "non-denial" (or good/valid) claim, the corresponding entry in the RVTO having diagnosis code as the row and procedure code as the column, has a numerical value. As the co-existences of that diagnosis code and procedure code occur more and more in "known" non-denial/good/valid insurance claims, the value of the entry corresponding to the intersection of that diagnosis code and procedure code in the cooccurrence matrix is higher. Thus, in this manner, the cooccurrence matrix models the associations between diagnosis codes and procedure codes in the set of "non-denial" (or good/valid) claims used to generate the RVTO.

Likewise, a cooccurrence matrix model could be used to describe the associations among diagnosis codes as both row and column of the matrix representing different diagnosis codes, for example, by indicating how often diagnosis codes appear together in the set of "non-denial" (or good/valid) claims used to generate the RVTO. A similar approach can be used to describe the association among procedure codes, thereby indicating how often procedure codes appear together in the set of "non-denial (or good/valid) claims used to generate the RVTO.

In some embodiments, the AI/ML model training is configured to reduce classification errors based on a predefined criterion through a regression process such as matrix factorization. By using a regression process, scenarios not a part of the "known" facts can be estimated or predicted by the RVTO. In operation, The RVTO provides query results which clearly distinguish "known" facts against "unknowns." For example, a query to the RVTO for the occurrence of diagnosis code $D_1$ and procedure code $P_1$ that returns a 0 from the cooccurrence matrix model represents that diagnosis code $D_1$ and procedure code $P_1$ have never appeared together in any of the known "non-denial" (or good/valid) claims that were used to generate the RVTO. Thus, an insurer is likely to deny payment of a new "unknown" claim that includes the combination of diagnosis code $D_1$ and procedure code $P_1$.

Block 123 includes a topic model created using the information in the RVTO from block 122. In some embodiments, the topic model comprises a Latent Dirichlet Allocation (LDA) Topic Model. However, other topic models and topic modeling approaches could be used.

An LDA topic model is an unsupervised model exploring the relationships among the terms and documents assuming Hierarchical Bayesian model relationships among the terms and documents. An LDA topic model can be trained using a set of collected documents consisting of terms for each document. In the insurance claim context, the documents for the LDA topic model are the individual insurance claims, and the terms for the LDA topic model are the features and codes in each individual claim, e.g., the diagnosis codes, feature codes, and other information contained in the claims. In practice, individual insurance claims that include the same set(s) of diagnosis and procedure codes (i.e., LDA terms) tend to share common characteristics and associations for individual patients.

In some embodiments, the LDA topic model classifies insurance claims (e.g., insurance claims in the RVTO) and takes the form of an N dimensional vector where N is a provisioned hyper-parameter selected by the topic model developer(s) to specify the number of topics the developers wish to have. For example, if a claim comprising p number of diagnosis codes and q number of procedure codes is input to an LDA topic model, the output of the LDA topic model is an n-dimensional vector. Such an input claim is generally classified to be in topic m when the $m^{th}$ component of the n-dimensional vector is the largest among all the components.

At block 124, the results and test vectors for test execution are compiled. Software executing in block 124 is configured to estimate the quality of the test vectors used (or perhaps to be used) in testing the AI/ML Engine of block 112. Some aspects of the test analyses performed at block 124 are described in more detail with reference to FIGS. 7 and 8.

FIG. 2 shows aspects of an example architecture 200 for testing an AI/ML Engine after initial deployment according to some embodiments. Example architecture 200 comprises a test execution environment for an AI/ML Engine that is under test for a post-deployment scenario. In operation, the example architecture 200 can be used to (i) measure the effectiveness of the testing, and (ii) identify candidates to be used to improve the AI/ML Engine and the Reference Virtual Test Oracle (RVTO).

Live claim data is received from healthcare service providers at block 201. Block 202 includes a deployed AI/ML Engine, which in practice is the same AI/ML Engine as in block 112 of FIG. 1(*a*). Block 203 includes a Reference Virtual Test Oracle, which in practice is the same RVTO as in block 122 of FIG. 1(*b*) and includes facts on collected information that was used to train the AI/ML Engine of block 202. Block 204 includes a topic model, such as an LDA Topic Model. In operation, the topic model of block 204 is functionally identical to the topic model of block 123 in FIG. 1(*b*), which in some embodiments is trained using collected and verified non-denial claims, i.e., trained with a set of insurance claims that are known to be "valid" or "good" claims that, if submitted to an insurer for payment, the insurer would likely pay the insurance claim.

Block 205 includes analysis software configured to perform output/result analysis. The claims and analysis results are forwarded from block 205 to both blocks 206 and 208. In operation, block 205 discovers new information which was not part of the training data selected from the collected information, i.e., "new" information that was not part of the insurance claims that were used for training the AI/ML model. The software functions executing in block 205 keep statistical account of the number of instances of various attributes in the live claim data provided to the AI/ML Engine for classification. These attributes include aspects of one or both of the learned training data and/or their topic model vector representation deviations, e.g. (i) for each live insurance claim input to the AI/ML Engine, whether the live claim is within a threshold similarity of an insurance claim in the training set of insurance claims associated with the same topic in the topic model as the live insurance claim, where the similarity is based on the one or more diagnosis codes of the live insurance code and the one or more diagnosis codes of the insurance claim in the training set, and (ii) for each topic in the topic model, an average topic vector of the live insurance claims associated with the topic, where the average topic vector for each topic is based at least in part on one or more of (a) how many live insurance claims are within the threshold similarity of at least one insurance claim in the training set of insurance claims associated with the same topic in the topic model as the live insurance claim, (b) how many live insurance claims are not within the threshold similarly of at least one insurance claim in the training set of insurance claims associated with the same topic in the topic model as the live insurance claim, (iii) how many live insurance claims the AI/ML Engine classified as valid (or "non-denial," i.e., "good" and, if submitted for payment, would likely be paid), and (iv) how many live insurance the AI/ML Engine classified as invalid (or "denial," i.e., "bad" and, if submitted for payment, would likely be denied payment).

These metrics, perhaps in combination with other metrics, help the AI/ML Engine operators identify how different the live data is from the data that was used to train the AI/ML Engine. Situations where the live data deviates too much from the training data can indicate that it may be advantageous to update (e.g., with supplemental training data) the AI/ML Engine in block 202 to help the AI/ML Engine better classify the live claim data from a particular source. Aspects of the procedure implemented in block 205 are described in more detail with reference to FIG. 9. Other data tracked and compiled at block 205 in some embodiments may additionally or alternatively include counters regarding the characteristics of the live claims, e.g., counters for the number of exact matches of the occurrence of the received live claims from the service provider per training claim data, counters for the number of occurrence of the unknown codes, counters for the number of re-occurrence of the same claim in the live claim on a per claim basis, counters for the number of re-occurrence of the same live claim on a per claim basis which results in a denial predicted by the AI/ML Engine, etc.

Software executing at block 206 is configured to process live claims that are flagged by the AI/ML Engine for potential denial. In operation, live claims flagged by the AI/ML Engine can be identified for additional review to correct the problems which caused the AI/ML Engine to classify the live claim as a "denial" claim. In some embodiments, the corrected live claim can additionally be validated at block 206. When a live claim is predicted by the AI/ML Engine to be a valid claim, the system at block 206 forwards the live claim to a payer (e.g., an insurance company) for payment. The information regarding the forwarded live claims is stored and maintained in a database, e.g., at block 206. In some embodiments, after classification by the AI/ML Engine, the claims can be further processed in block 208 when responses are received from the payer at block 207. In some embodiments, the analysis performed at block 205 is based at least in part on the classification returned by the AI/ML Engine whereas the analysis in block 208 is based on the action and validation from the payer. Based on the analysis in block 208, block 209 compiles candidates from the live claims that can be used to improve aspects of the AI/ML Engine and the RVTO.

FIG. 3 shows aspects of an example process 300 for generating a synthesized denial insurance claim using a known non-denial insurance claim according to some embodiments. In operation, each claim (i) has an associated LDA vector representation where n is the number of topics provisioned as a hyper-parameter, and (ii) includes a combination of one or more diagnosis codes and one or more procedure codes. The diagnosis codes and procedure codes are sometimes referred to herein as medical codes.

One type of denial (i.e., reason for classifying an insurance claim as "invalid" or "bad," such that, if submitted for payment to a payer, the payer will likely deny payment) is caused by an inconsistency among the procedure codes and the diagnosis codes contained in the insurance claim. For example, when a medical procedure corresponding to the procedure code(s) in an insurance claim does not match the treatment of the symptoms associated with the medical diagnosis corresponding to the diagnosis code(s) in the insurance claim, then a payer is likely to deny payment of the insurance claim. It is assumed that the training data represents a good knowledge base regarding valid claims (which would be paid) and invalid claims (which would be denied). One form of the knowledge base is the repository of all the training data. Other forms of the knowledge base include a medical code cooccurrence matrix model (e.g., an RVTO) and a topic model (e.g., a Latent Dirichlet Allocation (LDA) model).

In some LDA topic model implementations, when the highest component value is the $y^{th}$ component, the claim is categorized to be a member of topic y. At block 302, process 300 includes selecting a known non-denial claim belonging to topic y in the topic model. Then, at block 303, process 300 includes implementing one of a "remove," "replace," or "add" method to synthesize a denial claim from the selected known non-denial claim belonging to topic y in the topic model. In some embodiments, the selection performed at block 303 can be an exhaustive iterative selection, or a heuristic selection, or a random selection for each loop.

When the "remove" method is implemented at block 303, then at block 304, process 300 includes selecting a diagnosis code to be removed from the known non-denial claim (i.e., known valid claim) whose LDA vector representation shows that the diagnosis code belongs to a selected topic y, meaning that the diagnosis code's LDA vector representation has the highest value among all the components at y position. At block 305, process 300 includes synthesizing a denial claim by removing the selected diagnosis code from the known non-denial claim.

When the "replace" method is implemented at block 303, then at block 306, process 300 includes identifying a procedure code in the known non-denial claim (i.e., known valid claim) to be replaced by another procedure code identified at block 307. At block 0307, process 300 includes identifying a procedure code belonging to a different topic (e.g., topic z) such that the metric distance between topic y and topic z is equal to distance d, where d is within a provisioned value. Then, at block 308, process 300 includes synthesizing a denial claim using the known non-denial claim (i.e., known valid claim) selected in block 302 by replacing the identified procedure code in block 306 by the different procedure code identified in block 307. Intuitively, replacing a code by another code from a "far away" topic is easier than using a code from a "near-by" topic. However, replacing a code using a code from a "near-by" topic is more helpful to illustrate a differential contrast.

When the "add" method is implemented at block 303, then at block 309, process 300 includes identifying a procedure code from topic z such that topic y and topic z have a metric distance d, where d is within a provisioned value. Then, at block 310, process 300 includes synthesizing a denial claim using the known non-denial claim (i.e., known valid claim) selected at block 302 by adding the procedure code identified at block 309.

Next, at block 311, process 300 includes evaluating the synthesized denial claim using the Reference Virtual Test Oracle (RVTO) to confirm that the synthesized denial claim is truly different than the original known non-denial claim (i.e., known valid claim) that was selected in block 302 for use in generating the synthesized denial claim. At block 311, process 300 also includes evaluating the synthesized denial claim using the LDA topic model to produce an LDA topic vector for the synthesized denial claim. In some embodiments, the LDA topic vector for the synthesized denial claim can be used to validate that the remaining procedure code(s) in the synthesized denial claim is not associated with any of the diagnosis codes in the synthesized denial claim. This pair of the synthesized denial claim and the original known non-denial claim from which the synthesized denial claim was constructed is known as a differential pair. A metric distance is determined for this differential test pair to be the "differential gap" of the differential pair. At block 312, process 300 includes evaluating all the differential test pairs that were created based on a set of provisioned criteria as the test coverage. If the criteria are met, then the process ends.

In some embodiments, the metric distance between the original known non-denial claim from which the synthesized denial claim was constructed is based at least in part on a Kullback-Leibler (KL) Divergence or a variant on KL Divergence. In operation, the KL Divergence between a and b is asymmetric in that KL(a∥b) is not equal to KL(b∥a) where a and b are the vector representations of a particular topic or a particular claim for a set of LDA topics. In some embodiments, the metric distance between a and b, MD(a,b), is the average of KL(a∥b) and KL(b∥a). MD(a,b) using KL Divergence in the context of LDA Topic vector representation can be used to measure any one or more of (i) the distance between two topics in the topic model, (ii) the distance between two insurance claims (e.g., the distance between the synthesized denial claim and the original known non-denial claim from which the synthesized denial claim was constructed), and/or (iii) the distance between an insurance claim and a topic in the topic model. These distance measurements are used in connection with processes described with reference to FIG. 3, FIG. 4, and FIG. 5.

FIG. 4 shows aspects of an example process 400 for generating a synthesized non-denial insurance claim using a known denial insurance claim according to some embodiments. Process 400 shown in FIG. 4 is similar to process 300 in FIG. 3 in many respects except that process 400 illustrates a procedure for generating a synthesized non-denial ("good") claim from a known denial ("bad") claim whereas process 300 illustrates a process for generating a synthesized denial ("bad") claim from a known non-denial ("good") claim.

A block 402, process 400 includes selecting a known denial claim (i.e. a known "invalid" or "bad" claim that, if submitted to an insurer for payment, the insurer would likely deny payment) associated with a topic y in the topic model. Then, at block 403, process 400 includes implementing one of a "remove," "replace," or "add" method to synthesize a non-denial claim (i.e., a "valid" or "good" claim that, if submitted to an insurer for payment, the insurer would likely pay the claim) from the known denial claim.

When the "remove" method is implemented at block 403, process 400 advances to block 404, where process 400 includes selecting a procedure code to be removed from the known denial claim whose LDA vector representation shows that the selected procedure code does not belong to the selected topic y. Additionally at block 404, process 400 queries the RVTO to check the cooccurrence of the selected procedure code with all the diagnosis codes in the known denial claim. If all of the queried cooccurrence matrix entries are 0, this procedure code can be selected at block 404 for removal from the known denial claim. Then, a block 405, process 400 includes synthesizing the new non-denial claim (i.e., "valid" or "good" claim) using the known denial claim (i.e., "invalid" or "bad" claim) selected in block 402 by removing the procedure code selected in block 404 from the known denial claim.

When the "replace" method is implemented at block 403, process 400 advances to block 406, where process 400 includes identifying a procedure code in the known denial claim to be replaced by another procedure code identified at block 407. At block 406, process 400 includes identifying the first procedure code which does not have a cooccurrence matrix entry value shared with any of the diagnosis codes in the known denial claim selected at block 402. Then, at block 407, process 400 includes selecting a second procedure code which has a shared entry value larger than 0 with any of the diagnosis code(s) in the known denial claim according to the cooccurrence matrix in the RVTO. Then, at block 408, process 400 includes synthesizing the non-denial claim using the known denial claim selected at block 402 by replacing the first procedure code in the known denial claim with the second procedure code identified at block 407.

When the "add" method is implemented at block 402, process 400 advances to block 409, which includes selecting a diagnosis code which has a shared entry value with any of the procedure codes in the known denial claim or facts according to the cooccurrence matrix in the RVTO, but at the same time not a diagnosis code already appearing in the known denial claim selected at block 402. Then, at block 410, process 400 includes synthesizing the new non-denial claim using the known denial claim selected at block 402 by adding the procedure code identified at block 409.

Next, at block 411, process 400 includes evaluating the synthesized non-denial claim using the Reference Virtual Test Oracle (RVTO) to confirm that the synthesized non-denial claim is truly different from the known denial claim (i.e., known invalid claim) selected at block 402 for use in generating the synthesized non-denial (valid) claim. At block 411, process 400 also includes evaluating the synthesized non-denial claim by using the LDA topic model to produce an LDA topic vector for the synthesized non-denial claim. This pair of the synthesized non-denial claim (i.e., synthesized valid claim) and the original known denial claim (i.e., original invalid claim) from which the synthesized non-denial claim was constructed is known as a differential pair. A metric distance is determined for this differential pair to be the "differential gap" for the differential pair. At block 412, process 400 includes evaluating all the differential pairs that were created based on a set of provisioned criteria as the test coverage. If the test criteria are met, then process 400 ends.

As mentioned earlier, claims in the training dataset can be categorized into (or otherwise associated with) topics in an LDA topic model based on their LDA vector representation. The vector representation of a topic is the average vector representation of all the claims belonging to (or otherwise associated with) the topic. The average and maximum metric distance between all the claims in the topic is defined as the average radius and maximum radius of the topic.

Figure 5:
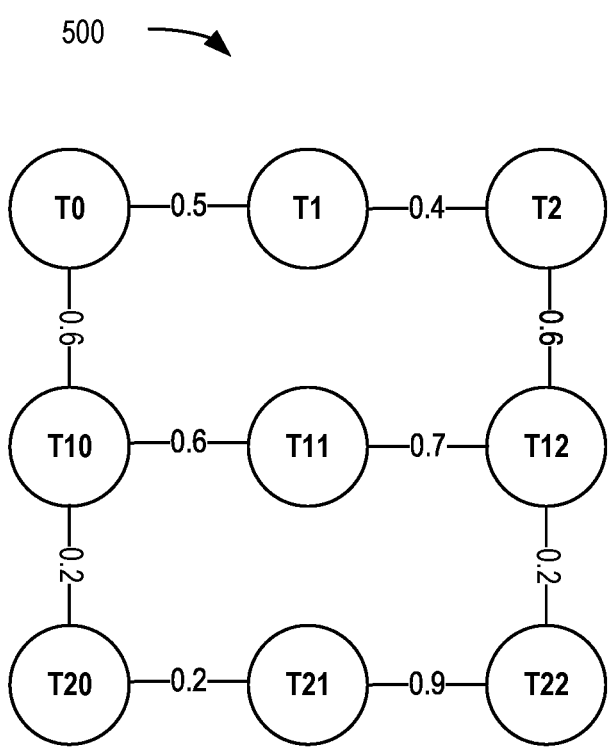
FIG. 5 shows aspects of an example topic map according to some embodiments.

FIG. 5 shows aspects of an example topic map 500 according to some embodiments. As shown in FIG. 5, a network of topics T0, T1, T2, T10, T11, T12, T20, T21, T22, and so on can be constructed. This network of topics is sometimes referred to herein as an LDA topic network and can be stored in a database (or other suitable data structure) for use in connection with the test quality analysis features implemented at block 113 of FIG. 1(*a*). This database provides a set of diagnosis codes and procedure codes for each topic in the topic model. As mentioned earlier, it is easier to synthesize a denial claim using a known non-denial claim by using a diagnosis or procedure code used by claims that are associated with a far-away topic. In some embodiments, the topic network 500 shown in FIG. 5 can be used as a guiding map in selecting a topic and code in connection with the synthesis procedure, e.g., in blocks 307 and 309 of process 300 shown in FIG. 3. The topic network 500 can also be used to evaluate the test coverage.

Figure 6:
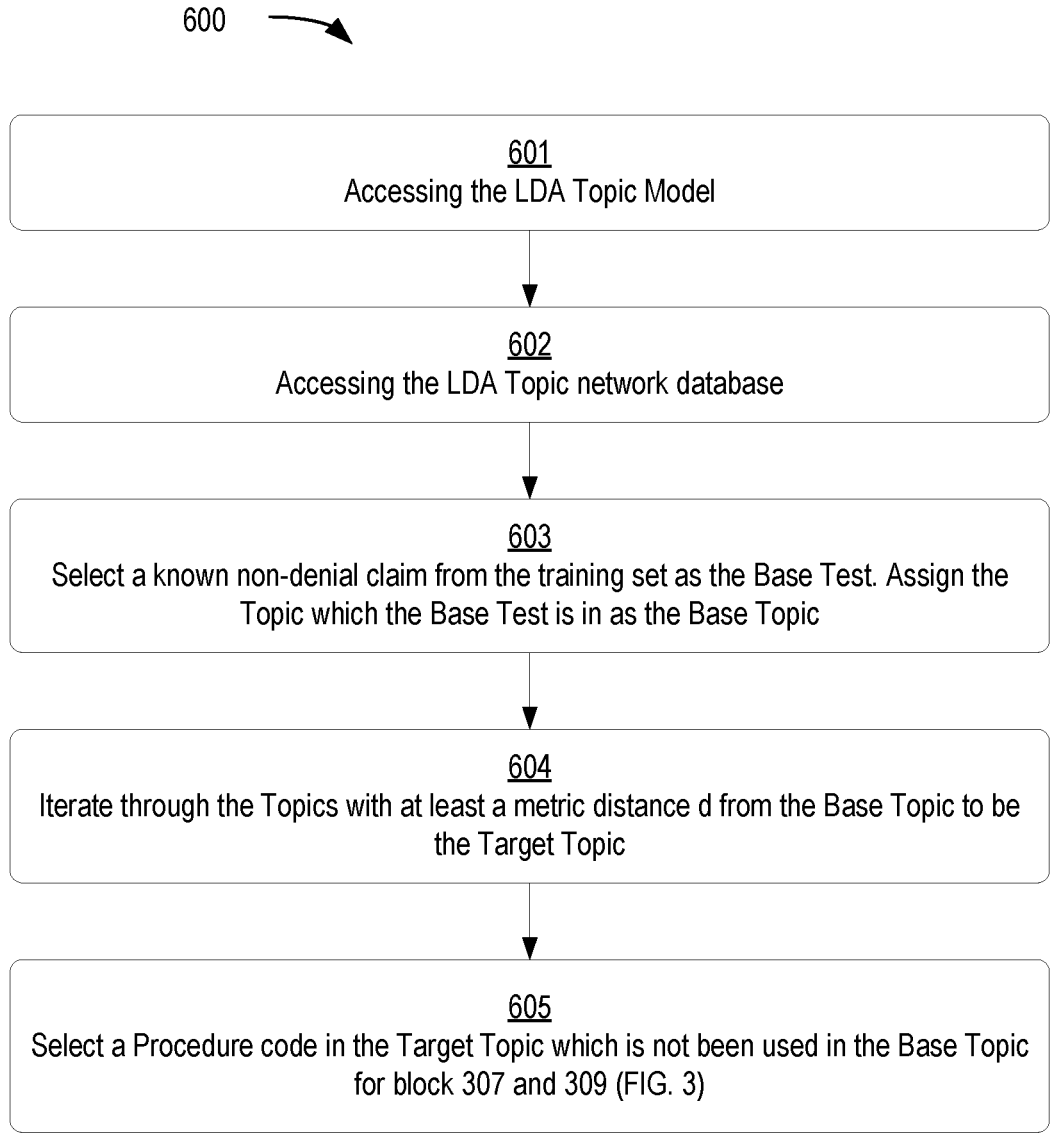
FIG. 6 shows aspects of an example process for generating synthesized insurance claims for testing an AI/ML Engine according to some embodiments.

FIG. 6 shows aspects of an example process 600 for generating synthesized insurance claims for testing an AI/ML Engine according to some embodiments. Example process 600 in FIG. 6 illustrates one way to select a procedure code, p, to replace an existing procedure code or to select a procedure code, p, to be added into a known non-denial claim for synthesizing a denial claim.

To identify a procedure code, p, we have to identify the LDA topic associated with the procedure code. A topic network database, like the one described with reference to FIG. 5 as an example, is derived using an LDA topic model. This database provides the relationships among different topics and their characteristics including an average LDA topic model vector presentation of all the topics, their average radius, and their maximum radius in metric distance. In some embodiments, the metric distance could use a variation of Kullback-Leibler (KL) Divergence. Since the KL Divergence between a and b is asymmetric in that KL(a||b) is not equal to KL(b||a), the metric distance between a and b, MD(a,b), in some embodiments is defined to be the average of KL(a||b) and KL(b||a).

As described earlier, some embodiments disclosed and described herein include synthesizing differential tests using known insurance claims. A high percentage of the known claims that are available for testing are non-denial claims that are used for AI/ML Engine training. At block 603, process 600 includes iterating through the known non-denial claims using one or more of exhaustive selection, random selection, pseudo-random selection, and/or heuristic selection to select a known non-denial claim for use in generating a synthesized denial claim. This known non-denial claim is referred to as a "base test" of a differential test pair.

A differential test pair includes two test vectors: (1) a base test (the known claim) and (2) a target test (the synthesized claim). The base test is a test which already exists from the collected claims. The target test is a test which is a synthesized test using the base test. Application of the base test and target test to the inputs of the Module Under Test (MUT) should produce different outcomes. In the context of insurance claim processing, the base test (the known claim) should result in a non-denial from the AI/ML Engine and the target test (the synthesized claim) should result in a denial from the AI/ML Engine. The metric distance between the base test and the target test is called the differential gap of the differential test pair. The topic for the base test is referred to as the base topic, and the topic for the target test is referred to as the target topic.

At block 604, process 600 includes selecting the target topic using the base topic. In some embodiments, a random selection algorithm can be used to identify a target topic with a metric distance at least d from the base topic.

At block 605, process 600 includes identifying a procedure code, p, to be used in blocks 307 and/or 309 of process 300 shown in FIG. 3. The procedure code, p, is selected from the target topic identified in block 604 in such a way that it does not appear in the base topic. The validity of the procedure code, p, selected at block 605 to replace another procedure code (e.g., at block 307 of process 300) or to be added into a claim (e.g., at block 309 of process 300) can also be validated using the RVTO as shown in block 311 of process 300 shown in FIG. 3.

Figure 7:
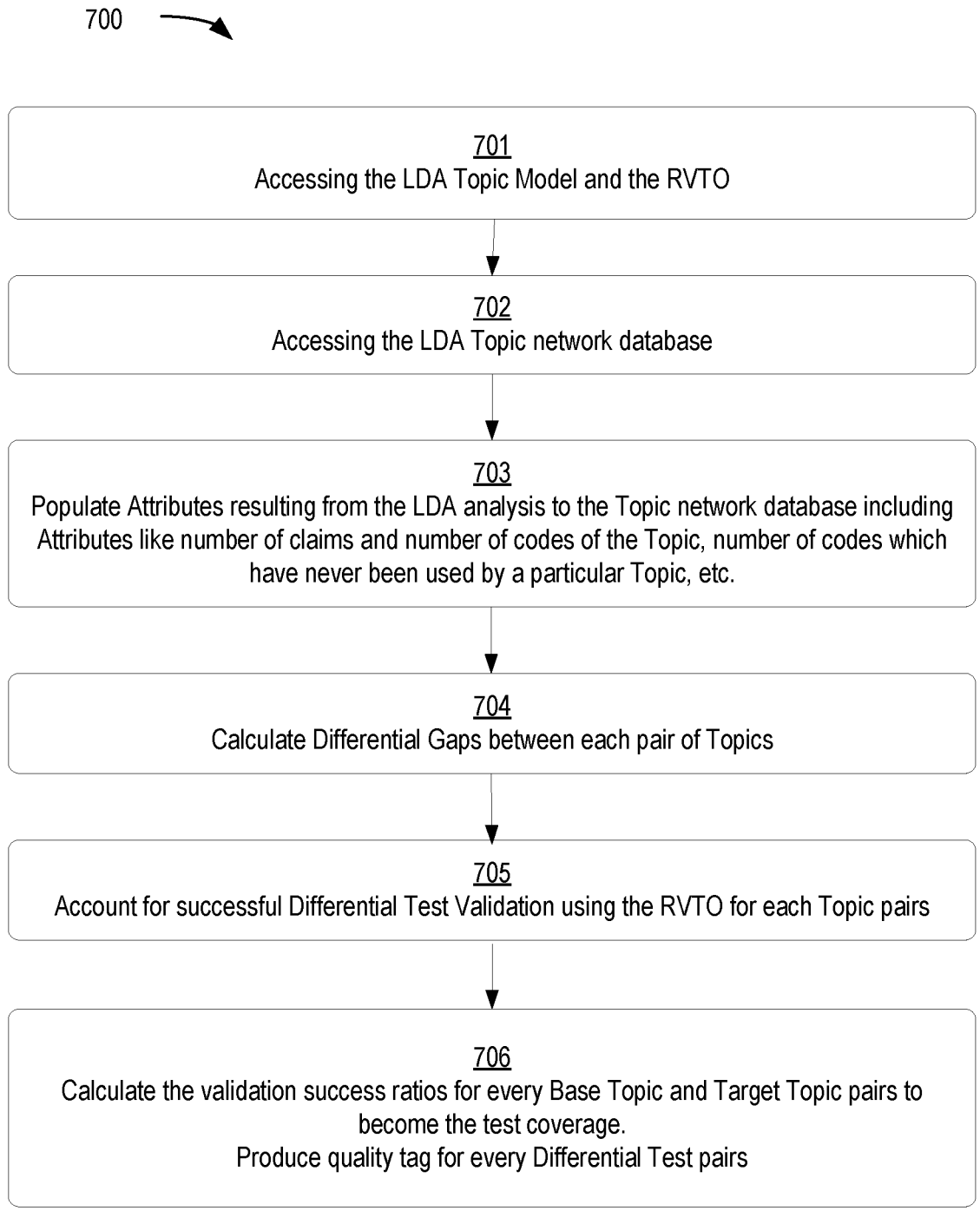
FIG. 7 shows aspects of an example process for assessing characteristics of synthesized test data according to some embodiments.

FIG. 7 shows aspects of an example process 700 for assessing characteristics of synthesized test data according to some embodiments. FIG. 7 illustrates the process of evaluating the synthesized differential tests in the pre-deployment scenario indicated in block 124. At block 701, process 700 includes accessing the LDA topic model and the RVTO. At block 702, process includes accessing the LDA topic network database.

Based on the LDA topic network database, the "base" number of the differential tests can be derived. Differential tests can be created using a known non-denial claim as the base (called the base claim or base test) and another claim (called the target test) using a code from another topic called the target topic. Thus, the base number, p, is defined to be j multiplied by k, where j is the number of codes in the target topic that do not appear in the base topic and k is the number of claims in the base topic. When the base topic and target topic are associated with the same topic, p becomes the sum of the number of codes used in all the claims associated with that topic. Test coverage is the ratio of the synthesized validated differential test over the sum of p values of all category pairs. Generally, the higher the percentage of the coverage, the better the quality of the test vectors that were produced. However, coverage percentage is not the only consideration.

Multiple differential tests can be synthesized from the same known case (or the same original claim). The objective is always to synthesize a "meaningful" opposite test (or claim) of the differential test pair using as little computing effort and resource as possible. In general, it is easier to synthesize a differential test pair with larger differential gap. However, when the differential gap is larger, semantically, it is less significant locally in the context of the test. For example, intuitively, for a non-denial claim related to kidney failure, it is easy to find a procedure code to be added into this non-denial claim resulting in a denial from a topic related to childbirth. However, it would take more effort and computing resources to find a procedure code from a topic related to high cholesterol to result in a denial because, in practice, the treatment of high cholesterol shares more diagnosis and procedure codes with kidney treatment. This can be observed by the metric distance between the topic(s) associated with kidney failure and the topic(s) associated with high cholesterol in the topic model. Since the metric distance between kidney disease and high cholesterol is closer (or more similar) in that they share more common diagnosis codes and procedure codes, it would take fewer resources (e.g., processing time) to identify a procedure code from childbirth to synthesize a denial claim from a kidney failure non-denial claim where the differential gap between kidney failure and childbirth is larger than the differential gap between kidney failure and high cholesterol. With limited computing resources, strategies can be derived to balance different objectives. For example, a user of the AI/ML Engine can specify the allowed differential gap range for use in connection with generating synthesized insurance claims.

At block 703, process 700 includes populating the information derived or obtained from the LDA topic model and the RVTO, including but not limited to the number of claims in a topic, the number of diagnosis codes and procedure codes used in a topic, the number of diagnosis codes or procedure codes that do not appear in another topic, etc. At block 704, process 700 includes enumerating all the topics at the base topic and the target topic as mentioned earlier to form a list of (Base Topic, Target Topic) pairs with their respective base number of differential tests. At block 705, process 700 includes categorizing all the validated differential tests using the RVTO according to the above mentioned (Base Topic, Target Topic) list from block 704. All the synthesized tests (or claims) can be validated using RVTO. At block 706, process 600 includes counting/tracking the number of successes, s, or failures, f, in validating the synthesized test pairs for each (Base Topic, Target Topic) pair. The ratio of s over p for each differential test pair is the test coverage for that differential test pair, and s divided by (s+f) is the test synthesis efficiency for that differential pair. In some embodiments, the differential test pairs with a differential gap less than the average topic radius are tagged as High Quality (HQ), the differential test pairs with a differential gap between the average and maximum topic radius are tagged as Medium Quality (MQ), the remaining differential test pairs are tagged Normal Quality (NQ) tests.

In some embodiments, in addition to the differential tests generated, a set of qualifying tests can also be used to detect false non-denials in the context of identifying potential denials for insurance claims. A false non-denial is a scenario where the AI/ML Engine classifies an insurance claim as "valid" (i.e., likely to be paid) when the claim is actually "invalid" (likely to be denied payment). A false non-denial could be easily experienced when modeling and training using sparse and ultra-high dimensional data. False non-denials can be caused by various reasons including random initialization, bias, normalization, sparsity of data and unknown truth. Once a false non-denial is detected, additional training data can be added to retrain the AI/ML Engine. Based on the cooccurrence matrix in the RVTO, certain occurrence combinations of a procedure code and a diagnosis codes represents a denial. Thus, a set of qualifying denial tests can be produced to detect gross false non-denials using simplified test claims that include a combination of a single diagnosis code and a single procedure code. The challenge is to produce a comprehensive test set covering all the corners of the ultra-high dimensional space evenly given availability of limited computing resources. In some embodiments, this can be accomplished by using LDA Topic Modeling and the process 800 shown in FIG. 8.

In practice, a claim with certain combinations of a diagnosis code and a procedure code results in a denial, so a procedure code that is only used by a topic paired with a diagnosis code that is only used by a different topic can produce a denial claim. This aspect of the insurance claims data provides a simple criterion when computing resources is a concern.

Figure 8:
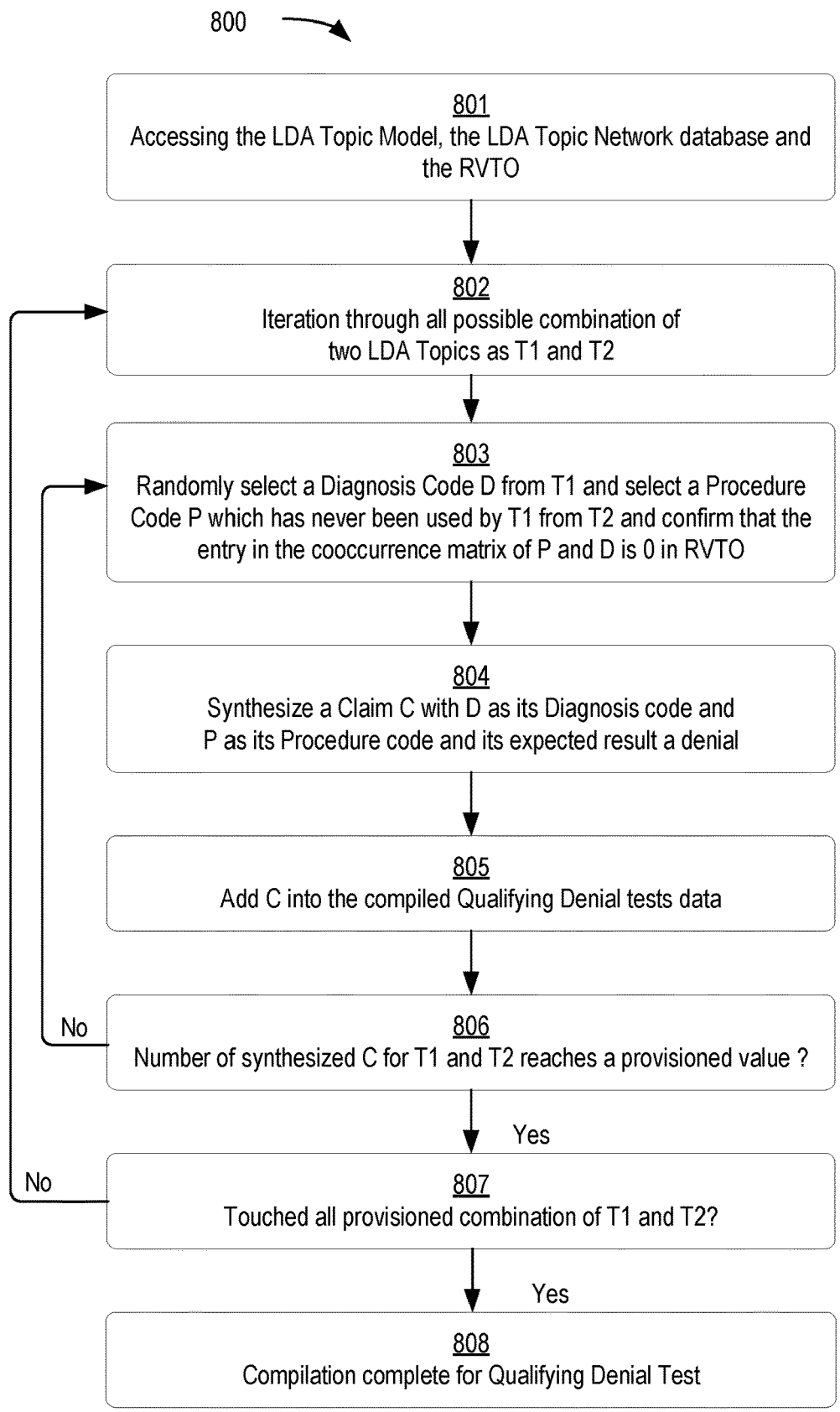
FIG. 8 shows aspects of an example process 800 for generating test data for qualifying denial conditions for insurance claim processing according to some embodiments.

FIG. 8 shows aspects of an example process 800 for generating test data for qualifying denial conditions for insurance claim processing according to some embodiments. At block 801, process 800 includes accessing the LDA topic model, LDA topic network database, and the RVTO. Via blocks 802 and 807, process 800 includes iterating through all the provisioned combinations of any two topics T1 and T2 in the topic network database.

At block 803, process 800 includes randomly selecting a diagnosis code, D, in T1 and a procedure code, P, used by at least one insurance claim associated with topic T2 but that does not appear in any insurance claim associated with topic T1. At block 803, process 800 also includes verifying that the entry value of P and D in cooccurrence matrix is 0 using the RVTO.

At block 804, process 800 includes synthesizing a new claim C using D and P with the expected result that the AI/ML Engine will classify new claim C as a denial. At block 805, process 800 includes adding the new verified denial claim C into a qualifying denial test set.

At block 806, process 800 includes checking whether a provisioned number of new claims has been synthesized for the combination of T1 and T2. And at block 808, process 800 completes the process of generating the Qualifying Denial Test by compiling the synthesized claims in to the qualifying denial test set.

Figure 9:
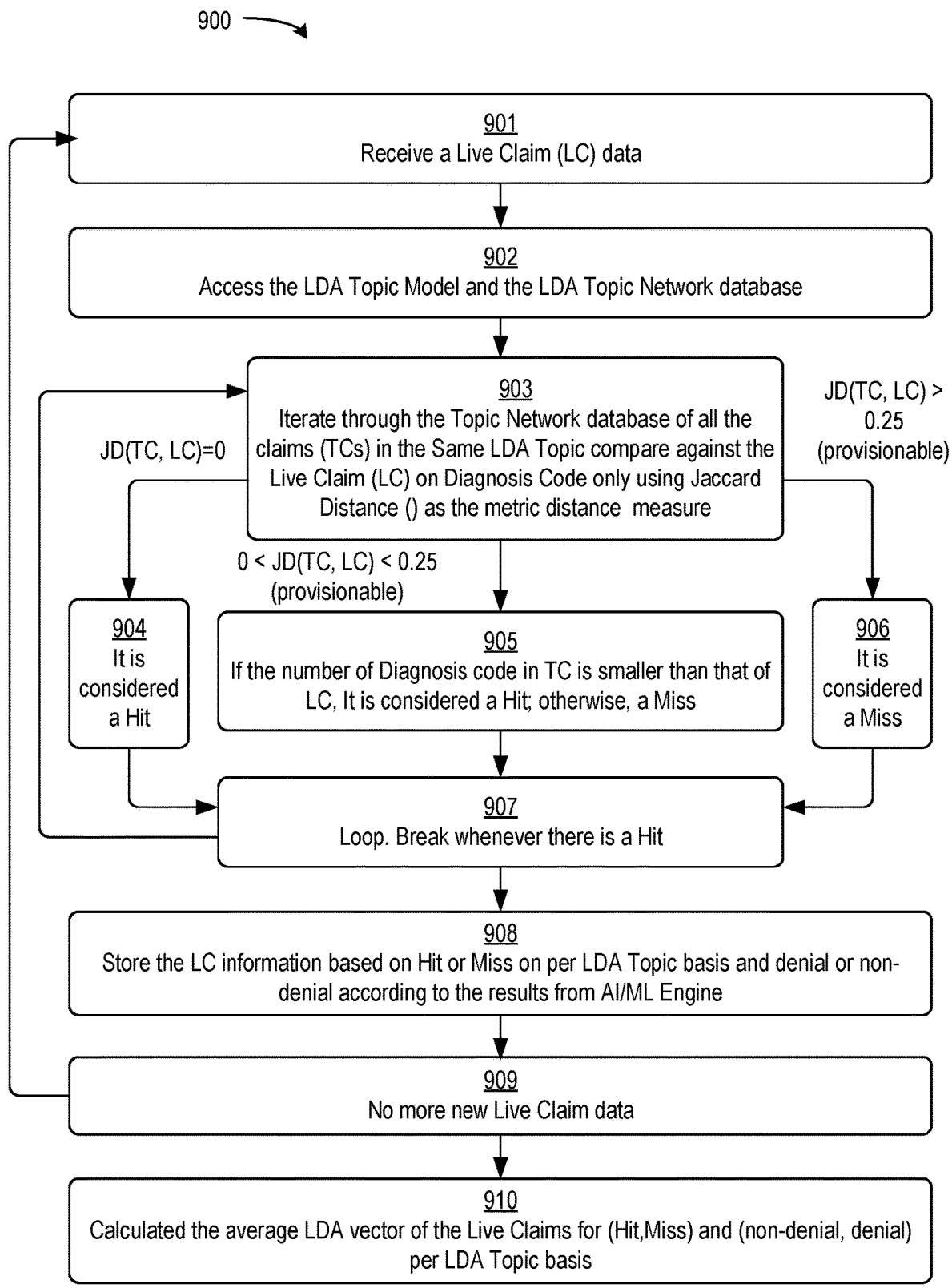
FIG. 9 shows aspects of an example process for analyzing post-deployment live insurance claims using metric distance according to some embodiments.

FIG. 9 shows aspects of an example process 900 for analyzing post-deployment live insurance claims using metric distance according to some embodiments, e.g., like in architecture 200 shown in FIG. 2. In operation, process 900 can be used to evaluate how relevant the training data are in classifying the received live claims. Since there are no pre-compiled results available for the live claims, the test loss cannot be evaluated. However, it is still important to evaluate whether the AI/ML Engine is trained to have sufficient knowledge to examine the live claims. When the live claims are within proximity of the training data, the AI/ML Engine is better able to classify those received claims more reliably than when the live claims are not within proximity of the training data. When the live claims are not within proximity of the training data, the live claims together with their respective responses from the payer can be selected for use in subsequent training the AI/ML Engine to improve the AI/ML Engine's ability to accurately classify live claims. Live claims that the AI/ML Engine classified as "valid" and that the payer paid (thereby confirming the AI/ML Engine's classification) can be added into the RVTO. In addition, live claims submitted to payer resulting in denial can also be used as future training data to improve the AI/ML Engine.

When a batch of live claims is received for classification by the AI/ML Engine, each live claim is examined individually using process 900.

At block 902, process 900 includes accessing the previously-prepared LDA topic model and the LDA topic network database.

At block 903, process 900 includes identifying each live claim's associated LDA topic, and then comparing the live claim against all the training data associated with the live claim's associated LDA Topic using a Jaccard Distance (JD) calculation.

The Jaccard Distance calculation, JD(A, B), measures dissimilarity between two sets A and B. JD(A,B)=size $[(A \cup B)-(A \cap B)]/\text{size}(A \cup B)$. For example, for A={I, j, k}, B={I, p, q}, then $(A \cup B)$={I, j, k, p, q} and $(A \cap B)$={I}. Thus, size$[(A \cup B)-(A \cap B)]$=size{j, k, p, q}=4 and size$(A \cup B)$=size{I, j, k, p, q}=5. This results in JD (A, B)=4/5=0.8.

When one of the insurance claims in the training data (the reference claim) associated with the LDA topic of the live claim has a Jaccard Distance of 0 with the live claim considering only the diagnosis codes in the live claim, it is considered a "Hit" in block 904. When the Jaccard Distance between the diagnosis codes of the reference claim and diagnosis codes of the live claim is less or equal than 0.25 (or some other provisioned value) but not 0 in block 905, at the same time, the number of diagnosis codes of the reference claim is smaller than the number of diagnosis codes of the live claim, it is considered a "Hit." Otherwise, it is a "Miss." When the Jaccard Distance is larger than 0.25 (or another provisioned value), it is a "Miss" in block 906. When the live claim (LC) finds a "Hit," the search process for this specific LC ends in block 907.

At block 908, process 900 includes keeping counters on Hit or Miss as statistical information of the LCs for every LDA Topic. Process 900 then moves to the next LC in this batch until all the live claims are processed in the batch.

At block 910, process 900 includes calculating the average LDA topic vectors of the live claims for all categories used in block 908. The result calculated at block 910 provides a good indicator of the effectiveness of the AI/ML Engine which is trained using the training data for screening this batch of live claims. When a live claim is identified as a miss, it is identified to become a candidate to be included in future training data to improve both the data stored in the RVTO and the effectiveness of the AI/ML Engine.

Figure 10:
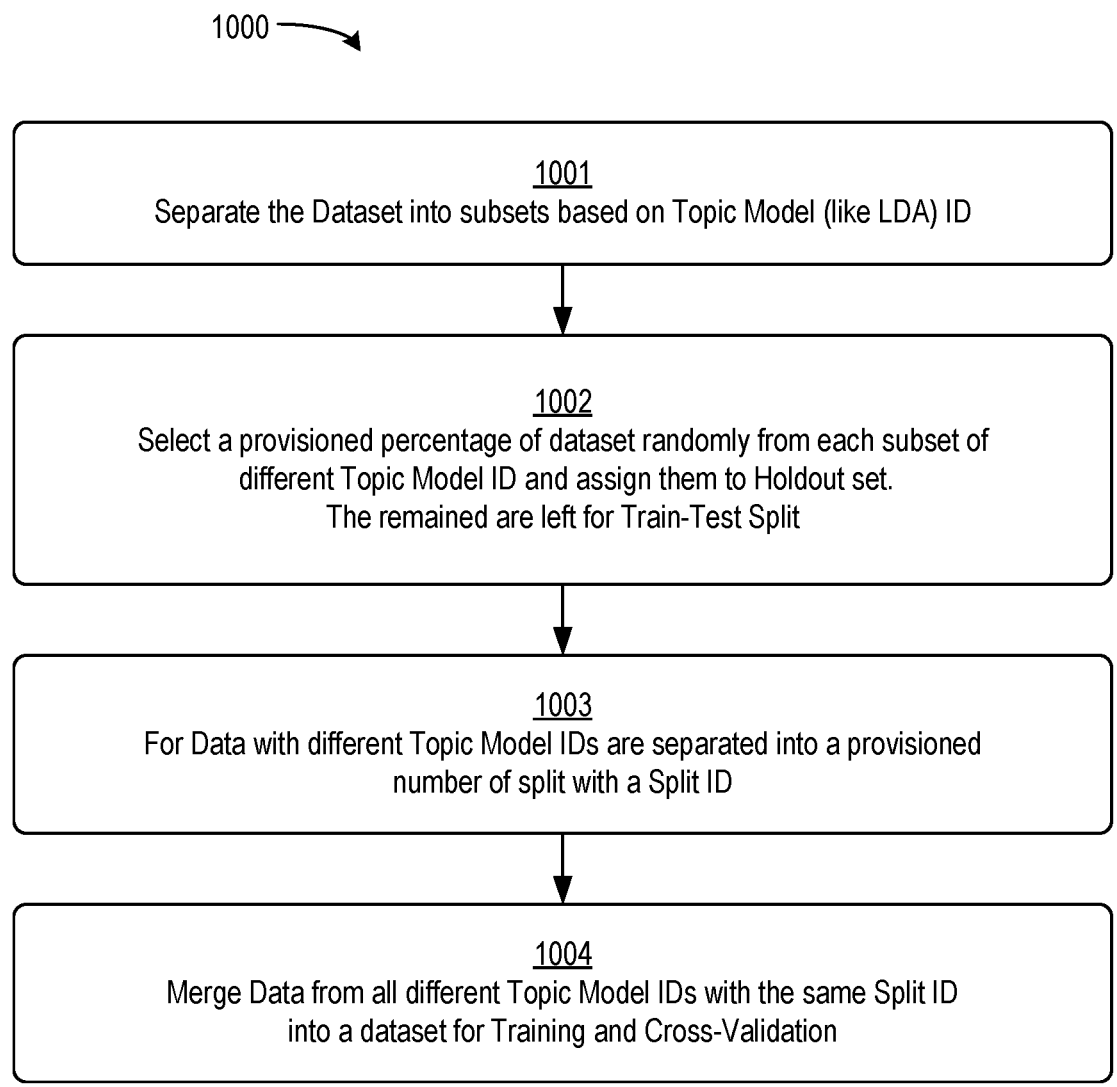
FIG. 10 shows aspects of an example process for performing train-test split and holdout test data selection according to some embodiments.

Additionally, the LDA model can be used as a part of a train-test split process. FIG. 10 shows aspects of an example process 1000 for performing train-test split and holdout test data selection according to some embodiments.

Traditionally, train-test split for cross-validation and holdouts is performed in a random manner. In some embodiments, at block 1001, process 1000 includes using LDA to analyze and categorize all the collected data into different subsets.

At block 1002, process 1000 includes assigning a provisioned percentage for split or holdouts as this percentage could be different from LDA topic to LDA topic (on a per subset basis). For example, the percentage could be higher for holdouts for LDA topics with a large number of claims while the percentage could be lower for holdouts for topics with fewer claims.

At block 1003, process 1000 includes performing a train-test split on a per LDA topic basis.

At block 1004, process 1000 includes merging the holdouts and the train-test splits from all the topics to produce the final holdouts and the train-test split into a dataset for further user in testing, training, and/or other purposes.

Figure 11:
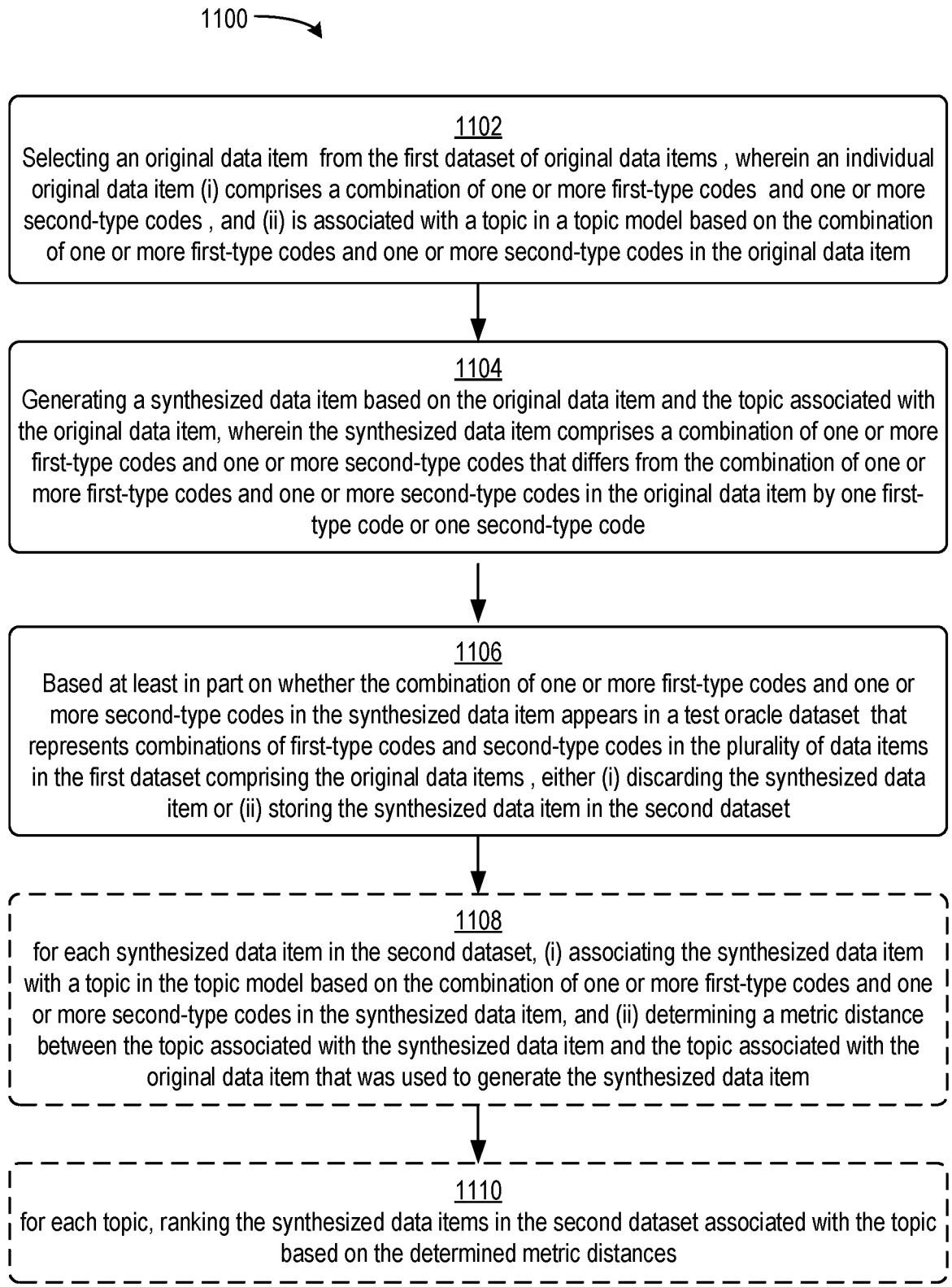
FIG. 11 shows a method for generating a second dataset comprising a plurality of synthesized data items from a first dataset comprising original data items according to some embodiments.

FIG. 11 shows a method 1100 for generating a second dataset comprising a plurality of synthesized data items from a first dataset comprising original data items according to some embodiments of the disclosed systems and methods. Aspects of method 1100 may be performed by one or more components of any of the architectures and/or processes disclosed and described herein.

Method 1100 begins at block 1102 which includes selecting an original data item from the first dataset of original data items, wherein an individual original data item (i) comprises a combination of one or more first-type codes and one or more second-type codes, and (ii) is associated with a topic in a topic model based on the combination of one or more first-type codes and one or more second-type codes in the original data item. In some embodiments, the topic model is or at least comprises a Latent Dirichlet Allocation Topic Model. Other suitable topic models could alternatively be used in addition to or instead of a Latent Dirichlet Allocation Topic Model.

In some embodiments, each data item in the second dataset comprising the plurality of synthesized data items is a healthcare insurance claim, each data item in the first dataset comprising the original data items is a healthcare insurance claim, each first-type code is a diagnosis code associated with a medical diagnosis, and each second-type code is a procedure code associated with a medical procedure. However, method 1000 has application beyond the generation of synthesized insurance claims. For example, method 1000 can be applied to any scenario where it is desirable to generate new testing data from existing data for use in testing and/or training artificial intelligence and/or machine learning systems, especially in scenarios where AI/ML Engines are used to classify ultra-high dimensional data.

At block 1104, method 1100 includes generating a synthesized data item based on the original data item and the topic associated with the original data item, wherein the synthesized data item comprises a combination of one or more first-type codes and one or more second-type codes that differs from the combination of one or more first-type codes and one or more second-type codes in the original data item by at least one first-type code and/or one second-type code.

At block 1106, method 1100 includes, based at least in part on whether the combination of one or more first-type codes and one or more second-type codes in the synthesized data item appears in a test oracle dataset that represents combinations of first-type codes and second-type codes in the plurality of data items in the first dataset comprising the original data items, either (i) discarding the synthesized data item or (ii) storing the synthesized data item in the second dataset. In some embodiments, the test oracle dataset is the same as or similar to the RVTO information systems disclosed and described herein. In some embodiments (i) discarding the synthesized data item or (ii) storing the synthesized data item in the second dataset at block 1106 includes for each topic in the topic model, tracking how many synthesized data items associated with that topic were discarded and how many synthesized data items associated with that topic were stored in the second dataset.

In some embodiments, method 1100 includes additional blocks 1108 and 1100.

At optional block 1108, method 1100 includes, for each synthesized data item in the second dataset, (i) associating the synthesized data item with a topic in the topic model based on the combination of one or more first-type codes and one or more second-type codes in the synthesized data item, and (ii) determining a metric distance between the topic associated with the synthesized data item and the topic associated with the original data item that was used to generate the synthesized data item.

At optional block 1110, method 1100 includes, for each topic, ranking the synthesized data items in the second dataset associated with the topic based on the determined metric distances.

In some embodiments, determining a metric distance between the topic associated with the synthesized data item and the topic associated with the original data item that was used to generate the synthesized data item in block 1108 includes: (i) determining a first Kullback-Leibler (KL) Divergence from the topic associated with the synthesized data item to the topic associated with the original data item that was used to generate the synthesized data item; (ii) determining a second KL Divergence from the topic associated with the original data item that was used to generate the synthesized data item to the topic associated with the synthesized data item; and (iii) setting the metric distance between the topic associated with the synthesized data item and the topic associated with the original data item that was used to generate the synthesized data item equal to an average of the first KL Divergence and the second KL Divergence.

In some embodiments, for each topic, ranking the synthesized data items in the second dataset associated with the topic based on the determined metric distances at block 1110 includes assigning a quality metric to each synthesized data item associated with the topic, wherein synthesized data items that have a shorter metric distance between the topic associated with the synthesized data item and the topic associated with the original data item from which the synthesized data item was generated have a higher quality metric than synthesized data items that have a longer metric distance between the topic associated with the synthesized data item and the topic associated with the original data item from which the synthesized data item was generated.

In some embodiments, block 1110 additionally includes creating a third dataset comprising a subset of the ranked synthesized data items in the second dataset, wherein an average of the determined metric distances of the synthesized data items in the third dataset is less than a threshold metric distance. Block 1110 may, in some embodiments, additionally include: (i) dividing the third dataset into a plurality of topic subsets, wherein each topic subset is associated with a different topic in the topic model; (ii) for each topic subset, randomly assigning a first percentage of the data items to a holdout set for the subset, and assigning a second percentage of the data items to a train-test split set, wherein a sum of the first percentage and the second percentage equals one hundred percent; (iii) combining the holdout sets into a combined holdout set comprising data items from each topic subset; (iv) combining the train-test split sets into a combined train-test split set comprising data items from each topic subset; (v) using a first portion of the train-test split set to train a machine learning model; (vi) using a second portion of the train-test split set for cross-validation; and (vii) using at least a portion of the combined holdout set to test the machine learning model. However, these additional features of block 1110 may, in some embodiments, be performed independently of other features implemented in method 1100.

In some embodiments, the step of generating a synthesized data item based on the original data item and the topic associated with the original data item at block 1104 includes at least one of (i) removing at least one first-type code or second-type code from the original data item, (ii) adding at least one first-type code or second-type code to the original data item, or (iii) replacing at least one second-type code in the original data item with a different second-type code.

In some embodiments, the original data item is known to be a valid data item and the original data item is associated with a first topic in the topic model.

In some embodiments where the original data item is known to be a valid data item and the original data item is associated with a first topic in the topic model, removing at least one first-type code or second-type code from the original data item comprises removing, from the one or more first-type codes in the original data item, a first-type code that contributes more than threshold weight to the association of the original data item with the first topic in the topic model.

Additionally, in some embodiments where the original data item is known to be a valid data item and the original data item is associated with a first topic in the topic model, adding at least one first-type code or second-type code to the original data item comprises adding, to the one or more second-type codes in the original data item, a new second-type code appearing in a data item associated with a topic other than the first topic. Preferably, the topic other than the first topic is a topic within a threshold metric distance from the first topic.

Also, in some embodiments where the original data item is known to be a valid data item and the original data item is associated with a first topic in the topic model, replacing at least one second-type code in the original data item with a different second-type code comprises replacing a second-type code in the original data item with a new second-type code appearing in a data item associated with a topic other than the first topic. Preferably, the topic other than the first topic is a topic within a threshold metric distance from the first topic.

Alternatively, in some embodiments, the original data item is known to be an invalid data item and the original data item is associated with a first topic in the topic model.

In some embodiments where the original data item is known to be an invalid data item and the original data item is associated with a first topic in the topic model, removing at least one first-type code or second-type code from the original data item comprises removing, from the one or more second-type codes in the original data item, a second-type code that both (i) contributes more than a threshold weight to associating data items with a topic in the topic model other than the first topic, and (ii) when removed, results in the synthesized data item comprising a combination of first-type codes and second-type codes appearing in the test oracle dataset.

Additionally, in some embodiments where the original data item is known to be an invalid data item and the original data item is associated with a first topic in the topic model, adding at least one first-type code or second-type code to the original data item comprises adding, to the one or more first-type codes in the original data item, a first-type code that both (i) contributes more than a threshold weight to associating data items with the first topic, and (ii) when added, results in the synthesized data item comprising a combination of first-type codes and second-type codes appearing in the test oracle dataset.

Also, in some embodiments where the original data item is known to be an invalid data item and the original data item is associated with a first topic in the topic model, replacing at least one second-type code in the original data item with a different second-type code comprises replacing a second-type code in the original data item with a new second-type code that both (i) contributes more than a threshold weight to associating data items with the first topic, and (ii) when added, results in the synthesized data item comprising a combination of first-type codes and second-type codes appearing in the test oracle dataset.

In some embodiments, method 1100 additionally includes generating a fourth dataset of data items. In such embodiments, the data items in the fourth dataset are configured to detect scenarios when a machine learning model erroneously identifies invalid data items as valid. In such embodiments, generating this fourth dataset of data items includes: (i) determining a set of topic-pairs from the topic model, wherein each topic-pair in the set of topic-pairs comprises a combination of two topics from the topic model; (ii) for each topic-pair, generating a topic-pair set comprising at least a configured quantity of new data items, wherein each new data item in the topic-pair set comprises (a) a first-type code associated with one topic of the topic-pair and (b) a second-type code associated with the other topic of the topic-pair, where a combination of the first-type code associated with the one topic of the topic-pair and the second-type code associated with the other topic of the topic-pair does not appear in any data item in the test oracle dataset; and (iii) combining all of the new data items into the fourth dataset comprising data items configured to detect scenarios where the machine learning model erroneously identifies invalid data items as valid. However, these additional features of block 1110 may, in some embodiments, be performed independently of other features implemented in method 1100.

In some embodiments, method 1100 additionally includes (i) receiving a batch of live data items for classification by a machine learning model, wherein each live data item (a) comprises a combination of one or more first-type codes and one or more second-type codes, and (b) is associated with a topic in a topic model; (ii) for each live data item, determining whether the live data item is within a threshold similarity of at least one data item in a training set of data items associated with the same topic in the topic model as the live data item, wherein the similarity is based on the one or more first-type codes of the live data item and the one or more first-type codes of the at least one data item in the training set of data items; and (iii) determining for each topic, an average topic vector of the live claims associated with the topic, wherein the average topic vector for each topic is based at least in part on one or more of (a) how many live data items were within the threshold similarity of at least one data item in a training set of data items associated with the same topic in the topic model as the live data item, (b) how many live data items were not within the threshold similarly of at least one data item in the training set of data items associated with the same topic in the topic model as the live data item, (c) how many live data items the machine learning model classified as valid, and (d) how many live data items the machine learning model classified as invalid. In some embodiments, determining whether the live data item is within a threshold similarity of at least one data item in the training set of data items associated with the same topic in the topic model as the live data item includes determining a Jaccard Distance between the live data item and each data item in the training set associated with the same topic in the topic model as the live data item until identifying the at least one data item in the training set that is within the threshold similarity. However, these additional features of block 1110 may, in some embodiments, be performed independently of other features implemented in method 1100.

The embodiments disclosed and described herein are intended to be examples for illustration purposes to help persons of skill in the art understand how to make and use the various combinations of features and functionality disclosed herein.

What is claimed is:

1. A method of generating a second dataset comprising a plurality of synthesized data items, wherein the plurality of synthesized data items are synthesized from a first dataset, wherein the first data set comprises a plurality of original data items, and wherein the method comprises:
   selecting a first original data item from the first dataset comprising the plurality of original data items, wherein the first original data item (i) comprises a combination of one or more first-type codes and one or more second-type codes, and (ii) is associated with a topic in a topic model based on the combination of the one or more first-type codes and the one or more second-type codes in the first original data item;
   generating a synthesized data item based on the first original data item and the topic associated with the first original data item, wherein the synthesized data item comprises a combination of one or more first-type codes and one or more second-type codes, wherein the combination of the first-type and the second-type codes of the synthesized data item differs from the combination of the one or more first-type codes and the one or more second-type codes in the first original data item by either (i) at least one first-type code or iii) at least one second-type code; and
   based at least in part on whether the combination of the one or more first-type codes and the one or more second-type codes in the synthesized data item appears in a test oracle dataset that represents combinations of first-type codes and second-type codes in the original data items in the first dataset comprising the plurality of original data items, either (i) discarding the synthesized data item or (ii) storing the synthesized data item in the second dataset.

2. The method of claim 1, further comprising:
   for each synthesized data item in the second dataset, (i) associating the synthesized data item with a topic in the topic model based on the combination of the one or more first-type codes and the one or more second-type codes in the synthesized data item, and (ii) determining a metric distance between the topic associated with the synthesized data item and the topic associated with the original data item that was used to generate the synthesized data item; and
   for each topic, ranking the synthesized data items in the second dataset associated with the topic based on the determined metric distances.

3. The method of claim 2, wherein for each synthesized data item in the second dataset, determining a metric distance between the topic associated with the synthesized data item and the topic associated with the original data item that was used to generate the synthesized data item comprises:

determining a first Kullback-Leibler (KL) Divergence from the topic associated with the synthesized data item to the topic associated with the original data item that was used to generate the synthesized data item;

determining a second KL Divergence from the topic associated with the original data item that was used to generate the synthesized data item to the topic associated with the synthesized data item; and setting the metric distance between the topic associated with the synthesized data item and the topic associated with the original data item that was used to generate the synthesized data item equal to an average of the first KL Divergence and the second KL Divergence.

4. The method of claim 2, wherein for each topic, ranking the synthesized data items in the second dataset associated with the topic based on the determined metric distances comprises:

assigning a quality metric to each synthesized data item associated with the topic, wherein synthesized data items that have a shorter metric distance between the topic associated with the synthesized data item and the topic associated with the original data item from which the synthesized data item was generated have a higher quality metric than synthesized data items that have a longer metric distance between the topic associated with the synthesized data item and the topic associated with the original data item from which the synthesized data item was generated.

5. The method of claim 2, further comprising creating a third dataset comprising a subset of the ranked synthesized data items in the second dataset, wherein an average of the determined metric distances of the synthesized data items in the third dataset is less than a threshold metric distance.

6. The method of claim 5, further comprising:

dividing the third dataset into a plurality of topic subsets, wherein each topic subset is associated with a different topic in the topic model;

for each topic subset, randomly assign a first percentage of the synthesized data items to a holdout set for the subset, and assign a second percentage of the synthesized data items to a train-test split set, wherein a sum of the first percentage and the second percentage equals one hundred percent;

combining the holdout sets into a combined holdout set comprising synthesized data items from each topic subset;

combining the train-test split sets into a combined train-test split set comprising synthesized data items from each topic subset;

using a first portion of the train-test split set to train a machine learning model;

using a second portion of the train-test split set for cross-validation; and using at least a portion of the combined holdout set to test the machine learning model.

7. The method of claim 1, wherein the topic model is a Latent Dirichlet Allocation Topic Model.

8. The method of claim 1, wherein generating a synthesized data item based on the first original data item and the topic associated with the first original data item comprises at least one of (i) removing at least one first-type code or second-type code from the first original data item, (ii) adding at least one first-type code or second-type code to the first original data item, or (iii) replacing at least one second-type code in the first original data item with a different second-type code.

9. The method of claim 8, wherein the first original data item is known to be a valid data item, wherein the first original data item is associated with a first topic in the topic model, and wherein removing at least one first-type code or second-type code from the first original data item comprises:

removing, from the one or more first-type codes in the original data item, a first-type code that contributes more than threshold weight to the association of the first original data item with the first topic in the topic model.

10. The method of claim 8, wherein the first original data item is known to be a valid data item, wherein the first original data item is associated with a first topic in the topic model, and wherein adding at least one first-type code or second-type code to the first original data item comprises:

adding, to the one or more second-type codes in the first original data item, a new second-type code appearing in a data item associated with a topic other than the first topic.

11. The method of claim 10, wherein the topic other than the first topic is a topic within a threshold metric distance from the first topic.

12. The method of claim 8, wherein the first original data item is known to be a valid data item, wherein the first original data item is associated with a first topic in the topic model, and wherein replacing at least one second-type code in the first original data item with a different second-type code comprises:

replacing a second-type code in the first original data item with a new second-type code appearing in a data item associated with a topic other than the first topic.

13. The method of claim 12, wherein the topic other than the first topic is a topic within a threshold metric distance from the first topic.

14. The method of claim 8, wherein the first original data item is known to be an invalid data item, wherein the first original data item is associated with a first topic in the topic model, and wherein removing at least one first-type code or second-type code from the first original data item comprises:

removing, from the one or more second-type codes in the first original data item, a second-type code that both (i) contributes more than a threshold weight to associating data items with a topic in the topic model other than the first topic, and (ii) when removed, results in the synthesized data item comprising a combination of first-type codes and second-type codes appearing in the test oracle dataset.

15. The method of claim 8, wherein the first original data item is known to be an invalid data item, wherein the first original data item is associated with a first topic in the topic model, and wherein adding at least one first-type code or second-type code to the first original data item comprises:

adding, to the one or more first-type codes in the first original data item, a first-type code that both (i) contributes more than a threshold weight to associating data items with the first topic, and (ii) when added, results in the synthesized data item comprising a combination of first-type codes and second-type codes appearing in the test oracle dataset.

16. The method of claim 8, wherein the first original data item is known to be an invalid data item, wherein the first original data item is associated with a first topic in the topic model, and wherein replacing at least one second-type code in the first original data item with a different second-type code comprises:

replacing a second-type code in the first original data item with a new second-type code that both (i) contributes more than a threshold weight to associating data items with the first topic, and (ii) when added, results in the synthesized data item comprising a combination of first-type codes and second-type codes appearing in the test oracle dataset.

17. The method of claim 1, further comprising generating a fourth dataset of data items, wherein data items in the fourth dataset are configured to detect scenarios when a machine learning model identifies invalid data items as valid, and wherein the method further comprises:

determining a set of topic-pairs from the topic model, wherein each topic-pair in the set of topic-pairs comprises a combination of two topics from the topic model;

for each topic-pair, generating a topic-pair set comprising at least a configured quantity of new data items, wherein each new data item in the topic-pair set comprises: (i) a first-type code associated with one topic of the topic-pair; and (ii) a second-type code associated with the other topic of the topic-pair, wherein a combination of the first-type code associated with the one topic of the topic-pair and the second-type code associated with the other topic of the topic-pair does not appear in any data item in the test oracle dataset; and combining all of the new data items into the fourth dataset comprising data items configured to detect scenarios where the machine learning model identifies invalid data items as valid.

18. The method of claim 1, further comprising:

receiving a batch of live data items for classification by a machine learning model, wherein each live data item (i) comprises a combination of one or more first-type codes and one or more second-type codes, and (ii) is associated with a topic in a topic model;

for each live data item, determining whether the live data item is within a threshold similarity of at least one data item in a training set of data items associated with a same topic in the topic model as the live data item, wherein the similarity is based on the one or more first-type codes of the live data item and the one or more first-type codes of the at least one data item in the training set of data items; and determining for each topic, an average topic vector of the live claims associated with the topic, wherein the average topic vector for each topic is based at least in part on one or more of (i) how many live data items were within the threshold similarity of at least one data item in a training set of data items associated with the same topic in the topic model as the live data item, (ii) how many live data items were not within the threshold similarly of at least one data item in the training set of data items associated with the same topic in the topic model as the live data item, (iii) how many live data items the machine learning model classified as valid, and (iv) how many live data items the machine learning model classified as invalid.

19. The method of claim 18, wherein determining whether the live data item is within a threshold similarity of at least one data item in the training set of data items associated with the same topic in the topic model as the live data item comprises:

determining a Jaccard Distance between the live data item and each data item in the training set associated with the same topic in the topic model as the live data item until identifying the at least one data item in the training set within the threshold similarity.

20. The method of claim 1, wherein (i) discarding the synthesized data item or (ii) storing the synthesized data item in the second dataset comprises:

for each topic in the topic model, tracking how many synthesized data items associated with that topic were discarded and how many synthesized data items associated with that topic were stored in the second dataset.

21. The method of claim 1, wherein each data item is a healthcare insurance claim, wherein each first-type code is a diagnosis code associated with a medical diagnosis, and wherein each second-type code is a procedure code associated with a medical procedure.

* * * * *